(12) United States Patent
Xu et al.

(10) Patent No.: US 9,895,273 B2
(45) Date of Patent: Feb. 20, 2018

(54) ABSORBENT ARTICLE AND RELATED METHODS

(71) Applicant: Little Nobleman Technology Limited, Hong Kong (HK)

(72) Inventors: Fei Xu, Hong Kong (HK); Sun Hoi Wong, Hong Kong (HK)

(73) Assignee: LITTLE NOBLEMAN TECHNOLOGY LIMITED, Hong Kong (HK)

( * ) Notice: Subject to any disclaimer, the term of this patent is extended or adjusted under 35 U.S.C. 154(b) by 0 days.

(21) Appl. No.: 15/389,445

(22) Filed: Dec. 22, 2016

(65) Prior Publication Data

US 2017/0258643 A1    Sep. 14, 2017

(30) Foreign Application Priority Data

Mar. 10, 2016 (HK) ................................ 16102762.4
Apr. 29, 2016 (HK) ................................ 16104923.6
Sep. 30, 2016 (CN) .......................... 2016 1 0872248

(51) Int. Cl.
   *A61F 13/15*    (2006.01)
   *A61F 13/42*    (2006.01)
   (Continued)

(52) U.S. Cl.
   CPC ........ *A61F 13/42* (2013.01); *A61F 13/49058* (2013.01); *B29C 66/45* (2013.01); *B29C 66/729* (2013.01); *B29C 66/742* (2013.01); *A61F 2013/421* (2013.01); *A61F 2013/422* (2013.01); *A61F 2013/423* (2013.01); *A61F 2013/424* (2013.01); *A61F 2013/426* (2013.01); *B29K 2023/06* (2013.01); *B29K 2105/256* (2013.01);
   (Continued)

(58) Field of Classification Search
   CPC ................ A61F 13/42; A61F 2013/423; A61F 2013/424; A61F 2013/426; A61F 2013/421; A61F 2013/422; A61L 14/56; A61B 5/6808; A61B 5/208; B29C 66/45; G01N 27/12; G01N 27/121; G08B 21/18
   USPC .................................................. 604/361, 362
   See application file for complete search history.

(56) References Cited

U.S. PATENT DOCUMENTS 4,610,678 A * 9/1986 Weisman .......... A61F 13/15203
                                                      604/368
5,469,145 A * 11/1995 Johnson .................. A61F 13/42
                                                      128/886
(Continued)

Primary Examiner — Jacqueline Stephens

(57) ABSTRACT

The present application relates to an electronic wetness-sensing absorbent article and related methods. The electronic wetness-sensing absorbent article includes a flexible waterproof thin film; at least two mutually separated and insulated flexible electrodes disposed on one surface of the flexible waterproof thin film; a water-permeable braided fabric layer; and an absorbent layer disposed on the other surface of the flexible waterproof thin film, located between the flexible waterproof thin film and the water-permeable braided fabric layer, and adapted to absorb a liquid entering from the water-permeable braided fabric layer. The flexible waterproof thin film, the flexible electrodes, and the liquid contained in the absorbent layer form a non-polar variable electrolytic capacitor. The wetness state of the electronic wetness-sensing absorbent article is obtained by detecting the capacitance value of the variable electrolytic capacitor and change thereof.

24 Claims, 14 Drawing Sheets

(51) Int. Cl.
*A61F 13/49* (2006.01)
*B29C 65/00* (2006.01)
B29K 105/00 (2006.01)
B29L 31/48 (2006.01)

(52) U.S. Cl.
CPC ............... *B29K 2995/0092* (2013.01); *B29K 2995/0093* (2013.01); *B29L 2031/4878* (2013.01)

(56) References Cited

U.S. PATENT DOCUMENTS

| | | | | |
|---|---|---|---|---|
| H001585 H | * | 8/1996 | Ahr | ............... A61F 13/53713 |
| | | | | 604/378 |
| 5,760,694 A | * | 6/1998 | Nissim | ............... A61F 13/42 |
| | | | | 128/885 |
| 2007/0255242 A1 | * | 11/2007 | Ales, III | ............... A61F 13/42 |
| | | | | 604/361 |
| 2013/0324955 A1 | * | 12/2013 | Wong | ............... G01N 27/223 |
| | | | | 604/361 |

\* cited by examiner

ABSORBENT ARTICLE AND RELATED METHODS

CROSS-REFERENCE TO RELATED APPLICATIONS

This application claims the benefit of Hong Kong short-term patent application Nos. 16102762.4 and 16104923.6 filed on Mar. 10, 2016 and Apr. 29, 2016, respectively, as well as Chinese patent application No. 201610872248.6 filed on Sep. 30, 2016; the contents of which are hereby incorporated by reference.

TECHNICAL FIELD

The present application relates to an absorbent article, and in particular, to a disposable liquid absorbent article capable of providing dynamic absorption process information and analyzing and manufacturing methods thereof.

RELATED ART

Disposable absorbent articles include paper diapers, nappies, paper urine pads, sanitary napkins and other absorbent articles. All the disposable absorbent articles have a problem of a need for timely replacement. If replacement is performed too frequently, it causes inconvenience and waste. However, late replacement may cause possible liquid leakage since the absorption capacity of an absorbent article is limited. How to dynamically detect and display an excretion condition of a user, including the number of times of excretion and excretion quantity, and whether the absorption capacity of an absorbent article has approached to saturation is of great reference value to the appropriate use of the absorbent article.

However, information provided by conventional wetness detection technology is limited. One of the most common technologies is to generate a wet prompt signal by short-circuiting two electrodes through urine. However, this wetness detection method in principle can only detect whether the urination has occurred instead of detecting the degree of wetness, let alone providing dynamic information of the urination process and the information about whether the absorption capacity of the absorbent article has approached to saturation. Thus, a new solution is required to solve the problem.

SUMMARY

In a first aspect, the present application provides an electronic wetness-sensing absorbent article capable of comprehensively providing wetness state information, including:

a flexible waterproof thin film;

at least two mutually separated and insulated flexible electrodes disposed on one surface of the flexible waterproof thin film;

a water-permeable braided fabric layer; and an absorbent layer disposed on the other surface of the flexible waterproof thin film, located between the flexible waterproof thin film and the water-permeable braided fabric layer, and adapted to absorb a liquid entering from the water-permeable braided fabric layer, wherein:

the flexible electrodes and the absorbent layer are located on the two surfaces of the flexible waterproof thin film respectively and are mutually separated and insulated from each other; and the flexible waterproof thin film, the flexible electrodes, and the liquid contained in the absorbent layer form a non-polar variable electrolytic capacitor, in which the flexible electrodes serve as electrodes of the electrolytic capacitor, the flexible waterproof thin film serves as a dielectric of the electrolytic capacitor, the liquid serves as an electrolyte of the electrolytic capacitor, and the wetness state of the electronic wetness-sensing absorbent article is obtained by detecting the capacitance value of the variable electrolytic capacitor and change thereof.

In another embodiment, in conjunction with any of the above and below embodiments, the absorbent layer may include a first absorbent and a second absorbent mixed in the first absorbent, the first absorbent is adapted to absorb the liquid entering from the water-permeable braided fabric layer and thus increase the capacitance value of the variable electrolytic capacitor, and the second absorbent is adapted to absorb the liquid from the first absorbent and thus reduce the liquid content in the first absorbent and the wet area of the first absorbent, so as to reduce the capacitance value of the variable electrolytic capacitor.

In another embodiment, in conjunction with any of the above and below embodiments, the absorption rate of the first absorbent is faster than that of the second absorbent, the liquid absorption capacity of the second absorbent is higher than that of the first absorbent, and the second absorbent has water absorption and retaining capacities, such that a process that the liquid migrates from the first absorbent to the second absorbent is realized; the process is dynamically reflected by the change of the capacitance value; and the first absorbent may include tiny water storage spaces formed by wood pulp or cotton pulp or a fluffy fabric or a flexible loose material, and the second absorbent may include a tiny granular macromolecular water-absorbing resin.

In another embodiment, in conjunction with any of the above and below embodiments, a hydrophilic layer may be disposed between the flexible waterproof thin film and the absorbent layer and at a position in close contact with the flexible waterproof thin film, the hydrophilic layer is adapted to absorb the liquid from the absorbent layer and maintains the surface area of the liquid covering the flexible electrodes unchanged, such that the change of the capacitance value of the variable electrolytic capacitor is reduced, and the hydrophilic layer includes any one or any combination of a hydrophilic material layer, a hydrophilic thin film, hydrophilic fibers, or a hydrophilic coating. A surfactant may also be disposed between the hydrophilic layer and the flexible waterproof thin film.

In another embodiment, in conjunction with any of the above and below embodiments, the flexible waterproof thin film is a flexible waterproof gas-permeable thin film, an anti-permeation coating is disposed between the flexible waterproof gas-permeable thin film and the hydrophilic layer and at a position in close contact with the surface of the water-permeable film, and the anti-permeation coating is adapted to prevent the liquid contained in the hydrophilic layer from leaking through the waterproof gas-permeable thin film, so as to avoid short-circuiting between the mutually separated and insulated flexible electrodes.

In another embodiment, in conjunction with any of the above and below embodiments, the flexible waterproof thin film may include a flexible insulating protective layer, covering the flexible electrodes and adapted to prevent the capacitance value of the electrolytic capacitor from being influenced when a human body touches the electrodes.

In another embodiment, in conjunction with any of the above and below embodiments, the flexible waterproof thin film may include a polyethylene thin film, and the water-permeable braided fabric layer may include a nonwoven fabric or a hot air nonwoven fabric.

In another embodiment, in conjunction with any of the above and below embodiments, the electronic wetness-sensing absorbent article may be any one of a paper diaper, a nappy, a paper urine pad, or a sanitary napkin.

In another embodiment, in conjunction with any of the above and below embodiments, the flexible electrodes may include wetness sensing lines printed on the flexible waterproof thin film using a carbon-based conductive ink.

In another embodiment, in conjunction with any of the above and below embodiments, the electronic wetness-sensing absorbent article may further include a wetness detection device, electrically connected to the wetness sensing lines and adapted to detect the wetness state of the electronic wetness-sensing absorbent article. The wetness detection device includes:

a charging and discharging unit, adapted to perform periodic charging and discharging operations on the wetness sensing lines disposed on the paper diaper;

a digital-to-analog conversion unit, adapted to obtain capacitance value data generated between the wetness sensing lines due to the periodic charging and discharging operations or voltage peak value data related to the capacitance value; and a processor, adapted to control the charging and discharging unit and the digital-to-analog conversion unit and process a series of voltage peak value data or capacitance value data to obtain quantified wetness state information.

In another embodiment, in conjunction with any of the above and below embodiments, the wetness detection device may further include:

a data information storage unit, adapted to store the series of voltage peak value data or capacitance value data and form a voltage curve or capacitance curve reflecting the wetness state of the electronic wetness-sensing absorbent article;

a valid-wetting determining unit, adapted to determine whether wetting occurs once, according to a drop of the voltage curve from an original value or a peak value or a rise of the capacitance curve from an original value or a valley value; and a wetness state output unit, adapted to output wetness state information of the electronic wetness-sensing absorbent article.

In another embodiment, in conjunction with any of the above and below embodiments, the wetness detection device may further include:

a dry-state determining unit, adapted to determine whether the electronic wetness-sensing absorbent article has changed back to the dry state, according to a rise of the voltage curve from a valley value or a drop of the capacitance curve from a peak value;

a wet count calculating unit, adapted to count the number of times of occurrence of wetting according to the output from the valid-wetting determining unit and output, when the number of times reaches a preset threshold, a signal indicating that the electronic wetness-sensing absorbent article needs to be replaced;

a wet-state duration calculating unit, adapted to calculate a time from a valley of the voltage curve or from a peak of the capacitance curve, and output a signal indicating that the electronic wetness-sensing absorbent article needs to be replaced, if the electronic wetness-sensing absorbent article has not changed back to the dry state when the time exceeds a preset threshold;

a wetness degree analyzing unit, adapted to determine a wetness degree of the electronic wetness-sensing absorbent article according to a dropping amplitude of the voltage curve or a rising amplitude of the capacitance curve, and output a signal indicating that the electronic wetness-sensing absorbent article needs to be replaced, when the change exceeds a preset threshold; and an excretion duration calculating unit, adapted to start timing from the occurrence of a valid wetness, and output a signal indicating that the electronic wetness-sensing absorbent article needs to be replaced, if there is no valid voltage valley or capacitance peak formed on the curve when a preset time threshold is reached.

In another embodiment, in conjunction with any of the above and below embodiments, the valid-wetting determining unit determines that wetting occurs once, when the voltage curve drops by 3%-30% from the original value or peak value.

In another embodiment, in conjunction with any of the above and below embodiments, the dry-state determining unit determines that the electronic wetness-sensing absorbent article has been restored to the dry state, when the voltage curves rises by 3%-30% from a valley.

In another embodiment, in conjunction with any of the above and below embodiments, the preset wet count threshold is in the range of 1-10 times, the preset wet-state duration threshold is in the range of about 1-60 min, the preset wetness degree threshold is in the range of a voltage value being 10%-90% of an original value, and the preset excretion time threshold is in the range of about 10-300 s.

In another embodiment, in conjunction with any of the above and below embodiments, the wetness detection device may further include:

a wireless transmission unit, adapted to send information related to the voltage peak value data in a wireless manner.

In another embodiment, in conjunction with any of the above and below embodiments, the electronic wetness-sensing absorbent article may be a paper diaper including an abdomen-side adhesive. The abdomen-side adhesive may include a Velcro-tape adapted to adhere the wetness detection device, and cuts are formed on two sides of the wetness sensing lines at an abdomen-side portion of the paper diaper, such that the wetness sensing lines can be overturned by means of the cuts so as to electrically connect to the wetness detection device.

In another embodiment, in conjunction with any of the above and below embodiments, the electronic wetness-sensing absorbent article may be a paper diaper including an abdomen-side adhesive. The abdomen-side adhesive may include a Velcro-tape adapted to adhere the wetness detection device, and the paper diaper may include a projecting portion at the wetness sensing lines at the abdomen-side portion of the paper diaper, and the projecting portion is adapted to be overturned for electrically connecting the wetness sensing lines to the wetness detection device.

In another embodiment, in conjunction with any of the above and below embodiments, the wetness detection device may further include:

a rear housing, provided with a Velcro-tape adapted to adhesively fasten the wetness detection device to the electronic wetness-sensing absorbent article;

a front housing, forming a sealed body together with the rear housing;

an electronic circuit board, located inside the sealed body;

a movable latch, adapted to tightly fasten the electronic wetness-sensing absorbent article in cooperation with the front housing; and probes, one end of each being located between the front housing and the movable latch, wherein when the electronic wetness-sensing absorbent article is tightly fastened, the probes are electrically connected to the wetness sensing lines on the electronic wetness-sensing absorbent article, so as to obtain a variable capacitance value signal provided by the electronic wetness-sensing absorbent article and send the variable capacitance value signal to the electronic circuit board.

In another embodiment, in conjunction with any of the above and below embodiments, the wetness detection device may further include:

a housing opening groove, through which the front housing can be separated from the rear housing for a battery replacement.

In another embodiment, in conjunction with any of the above and below embodiments, the wetness detection device may further include:

a housing seal ring, located between the front housing and the rear housing, and adapted to form a seal between the front housing and the rear housing; and a probe seal ring, located between the probes and the front housing, and adapted to form a seal between the probes and the front housing.

In another embodiment, in conjunction with any of the above and below embodiments, the wetness detection device may be of a flat circular structure having a diameter in the range of about 15-50 mm and a thickness in the range of about 5-20 mm.

In another embodiment, in conjunction with any of the above and below embodiments, the wetness detection device may further include:

a diaper-fastening detection unit, adapted to determine whether the electronic wetness-sensing absorbent article is tightly fastened by the movable latch, wherein when at least two of the probes are in contact with a same wetness sensing line at the same time, the diaper-fastening detection unit sends a diaper-fastened signal and turns on a light emitting diode (LED) indicator thereon.

In another embodiment, in conjunction with any of the above and below embodiments, the wetness detection device may further include a sleep posture detection unit, adapted to send a prone position signal when the wetness detection device is overturned.

In another embodiment, in conjunction with any of the above and below embodiments, the wetness sensing lines extend across the electronic wetness-sensing absorbent article, the width of the wetness sensing lines is in the range of about 3-15 mm, and the spacing between adjacent wetness sensing lines is in the range of about 3-15 mm.

In another aspect, the present application provides a method of manufacturing a disposable absorbent article capable of providing dynamic liquid absorption process information and absorption capacity information, including the following steps:

selecting a flexible waterproof thin film as a substrate;

disposing at least two mutually separated and insulated flexible electrodes on one surface of the waterproof thin film;

covering the electrodes with a flexible insulating layer;

disposing a first absorbent at a position, directly opposite to the electrodes, on the other surface of the waterproof thin film;

disposing a second absorbent above the first absorbent or mixing the second absorbent in the first absorbent, the second absorbent having strong water absorption and retaining capacities, the first absorbent and the second absorbent forming an absorbent layer of the electronic wetness-sensing absorbent article;

covering the absorbent layer with a water-permeable braided fabric layer, so that the absorbent layer is fixed between the waterproof thin film and the water-permeable braided fabric layer;

forming, through the above configuration, a disposable absorbent article in which a liquid injected from the water-permeable braided fabric is absorbed by the first absorbent and then absorbed and locked by the second absorbent from the first absorbent and is prevented from leakage by means of the waterproof thin film; and forming a special non-polar variable electrolytic capacitor by the electrodes, the waterproof thin film, and the liquid contained in the first absorbent, wherein the flexible electrodes serve as electrodes of the electrolytic capacitor, the waterproof thin film serves as a dielectric of the electrolytic capacitor, the liquid contained in the first absorbent serves as an electrolyte of the electrolytic capacitor; the capacitance value of the electrolytic capacitor is related to the content and distribution of the electrolyte contained in the first absorbent, and the process that the liquid enters the first absorbent from the water-permeable braided fabric layer and is then absorbed and locked by the second absorbent from the first absorbent is dynamically reflected by the change of the capacitance value of the electrolytic capacitor.

In another embodiment, in conjunction with any of the above and below embodiments, the manufacturing method may further include the following step:

disposing a material layer or coating with a particular hydrophilic or hydrophobic property between the waterproof thin film and the first absorbent and at a position in close contact with the surface of the waterproof thin film, wherein the hydrophilic or hydrophobic property of the material has impact on the accumulation and distribution of the liquid in the first absorbent on the surface of the waterproof thin film, and therefore has impact on the change of the capacitance value of the electrolytic capacitor, leading to the formation of different patterns of capacitance change and the content or distribution state of the liquid of the first absorbent is obtained by detecting the capacitance value of the capacitor.

In another embodiment, in conjunction with any of the above and below embodiments, the first absorbent has a faster but lower absorption capacity, the liquid entering from the water-permeable braided fabric layer is firstly reflected by an increase in the liquid content in the first absorbent, such that the capacitance value of the electrolytic capacitor is increased;

the second absorbent has a slower but higher liquid absorption capacity, and captures the liquid from the first absorbent and locks the liquid, such that the water content in the first absorbent is reduced, and the capacitance value of the electrolytic capacitor is reduced, thus forming a dynamic change process that the capacitance value first increases and then decreases; and the water absorption and retaining capacities of the second absorbent are limited, and the water absorption and retaining capacities decease significantly when approaching to saturation, such that the ability of the second absorbent to capture the liquid from the first absorbent is lowered, and the decreasing speed of the capacitance value is reduced, thereby providing information about whether the liquid absorption and retaining capacities of the electronic wetness-sensing absorbent article approach to a limit.

In another embodiment, in conjunction with any of the above and below embodiments, the electronic wetness-sensing absorbent article may be a disposable paper diaper, a nappy, a paper urine pad, and a sanitary napkin; the waterproof thin film may include a polyethylene thin film; the water-permeable braided fabric may include a nonwoven fabric and a hot air nonwoven fabric; the flexible electrodes may include conductive ink lines printed on the waterproof thin film and metal lines adhered to the waterproof thin film; the insulating layer covering the electrodes may include a soft and loose nonwoven fabric and a spunbonded fabric; the first absorbent may include tiny water storage spaces formed by wood pulp or cotton pulp or a fluffy fabric or a particular flexible material, and the second absorbent may include a tiny granular macromolecular water-absorbing resin mixed in the first absorbent or embedded in the tiny water storage spaces; the hydrophilic material may include paper, cotton, and hydrophilic fibers; the hydrophobic material may include a nonwoven fabric, hydrophobic fibers and a surfactant; and the liquid may include urine, sweat, menstruation, or other water-containing excrements from human bodies or animals.

In still another aspect, the present application relates to a method for realizing wetness analysis and state prompting on the basis of the abovementioned electronic wetness-sensing absorbent article, including the following steps:

performing periodic charging and discharging on the electrodes of the electronic wetness-sensing absorbent article to obtain a series of capacitance value information or voltage information related to the capacitance value that is presented between the electrodes, the voltage or capacitance information data forming a dynamic voltage or capacitance curve containing wetness state information of the electronic wetness-sensing absorbent article;

analyzing the curve to find peak values and valley values in the curve;

presetting a wetness determining voltage or capacitance threshold;

determining the occurrence of a valid wetness, when the voltage curve drops from a peak value or the capacitance curve rises from a valley value and the drop or rise reaches the preset threshold;

presetting a dry restoration voltage or capacitance threshold;

determining that the electronic wetness-sensing absorbent article has changed back to the dry state, when the voltage curve rises from a valley value and reaches the preset threshold or the capacitance curve drops from a peak value and reaches the preset threshold;

presetting a wet count threshold; and sending a signal indicating that the electronic wetness-sensing absorbent article needs to be replaced, when the number of times of occurrence of valid wetting reaches the preset threshold.

In another embodiment, in conjunction with any of the above and below embodiments, the method may further include the following steps:

presetting a minimum voltage threshold or a maximum capacitance threshold;

deeming that the electronic wetness-sensing absorbent article has reached a maximum wetness degree and sending a signal indicating that the electronic wetness-sensing absorbent article needs to be replaced, when the voltage curve drops to the preset minimum voltage threshold or the capacitance curve rises to the preset maximum capacitance value;

presetting a maximum wait-time-to-dryness threshold;

deeming that the water absorption and retaining capacities of the second absorbent have approached to saturation and sending a signal indicating that the electronic wetness-sensing absorbent article needs to be replaced, when the voltage curve is in a valley or the capacitance curve is in a peak and the electronic wetness-sensing absorbent article cannot change back to the dry state within a preset period of time;

presetting a maximum liquid excretion time threshold; and starting timing from the occurrence of a valid wetness, and if there is no valid valley formed on the voltage curve or no valid peak formed on the capacitance curve when the preset time threshold is reached, deeming that the excretion time is unduly long or the water absorption and retaining capacities of the second absorbent have approached to saturation, and sending a signal indicating that the electronic wetness-sensing absorbent article needs to be replaced.

In yet another aspect, the present application is directed to a detection system for implementing the wetness analysis and state prompting method, including:

a charging and discharging device, adapted to implement periodic charging and discharging operations on the electrodes;

a digital-to-analog conversion unit, adapted to obtain a series of capacitance value data information or a series of voltage peak value data information related to the capacitance value of the electronic wetness-sensing absorbent article, which is generated between the electrodes due to the periodic charging and discharging operations;

a data information storage unit, adapted to store the series of voltage peak value data information or capacitance value data information, and form a dynamic voltage or capacitance curve reflecting the wetness state of the electronic wetness-sensing absorbent article;

a valid-wetting determining unit, adapted to determine through analysis whether valid wetting occurs once, according to a drop of the voltage curve from an original value or a peak value or a rise of the capacitance curve from an original value or a valley value;

a wetness state output unit, adapted to output state information or data related to the wetness state of the electronic wetness-sensing absorbent article; and a processor, adapted to connect to, contain, or control the related units and implement the related functions.

In another embodiment, in conjunction with any of the above and below embodiments, the detection system may further include:

a dry-state determining unit, adapted to determine whether the electronic wetness-sensing absorbent article has changed to the dry state, according to a rise of the voltage curve from a valley value or a drop of the capacitance curve from a peak value;

a wet count calculating unit and a wet count threshold storage unit, adapted to count the number of times of occurrence of wetting of the electronic wetness-sensing absorbent article according to the output from the valid-wetting determining unit, and send a signal indicating that the electronic wetness-sensing absorbent article needs to be replaced, when the number of times reaches the preset threshold;

a wet-state duration calculating unit and a maximum wait-time-to-dryness threshold storage unit, adapted to calculate a time from a valley of the voltage curve or from a peak of the capacitance curve, and send a signal indicating that the electronic wetness-sensing absorbent article needs to be replaced, if the electronic wetness-sensing absorbent article has not changed back to the dry state when the time exceeds the preset threshold;

a wetness degree analyzing unit and a minimum voltage threshold or maximum capacitance threshold storage unit, adapted to deem a dropping amplitude of the voltage curve or a rising amplitude of the capacitance curve as a wetness degree of the electronic wetness-sensing absorbent article, and send a signal indicating that the electronic wetness-sensing absorbent article needs to be replaced, when the value change reaches a preset threshold; and an excretion duration calculating unit and a maximum excretion time threshold storage unit, adapted to start timing from the occurrence of a valid wetness, and if there is no valid voltage valley or capacitance peak formed on the curve when the preset time threshold is reached, deem that the excretion time is unduly long or the water absorption and retaining capacities of the second absorbent have approached to saturation, and send a signal indicating that the electronic wetness-sensing absorbent article needs to be replaced.

In another embodiment, in conjunction with any of the above and below embodiments, the wetness determining voltage threshold may be 70%-97% of the original value or peak value of the voltage curve, and it is determined the occurrence of a valid wetness when the voltage curve drops by 3%-30% from the original value or peak value;

the dry restoration voltage threshold may be 103%-130% of the valley value of the voltage curve, and it is determined that the electronic wetness-sensing absorbent article is in the dry state when the voltage curve rises by 3%-30% from the valley;

the maximum wait-time-to-dryness threshold is 1-60 min;

the maximum excretion time threshold is 10-300 s;

the wet count threshold is 1-10 times; and the minimum voltage threshold is 10%-90% of the original voltage value.

In another embodiment, in conjunction with any of the above and below embodiments, the detection system may include a smart phone capable of receiving a Bluetooth signal, and the wetness state output unit may include a Bluetooth or wireless fidelity (Wi-Fi) transceiver capable of sending a series of voltage peak value data information or capacitance value information related to the wetness state of the electronic wetness-sensing absorbent article to the smart phone via Bluetooth or Wi-Fi; and the data information storage unit, the valid-wetting determining unit, the dry-state determining unit, the wet count calculating unit, the wet count threshold storage unit, the wet-state duration calculating unit, the maximum wait-time-to-dryness threshold storage unit, the wetness degree analyzing unit, the minimum voltage threshold or maximum capacitance threshold storage unit, the excretion duration calculating unit, and the maximum excretion time threshold storage unit are all disposed in the smart phone, the related functions are implemented by a combination of hardware and software; or the detection system may include a wireless receiver and state display, and the wetness state output unit may include a wireless transmitter capable of sending a series of voltage peak value data information or capacitance value information related to the wetness state of the electronic wetness-sensing absorbent article to the wireless transceiver and state display; and the data information storage unit, the valid-wetting determining unit, the dry-state determining unit, the wet count calculating unit, the wet count threshold storage unit, the wet-state duration calculating unit, the maximum wait-time-to-dryness threshold storage unit, the wetness degree analyzing unit, the minimum voltage threshold or maximum capacitance threshold storage unit, the excretion duration calculating unit, and the maximum excretion time threshold storage unit are all disposed in the wireless receiver and state display, and the related functions are implemented by a combination of hardware and software.

The present application shows the following beneficial effects: by disposing the flexible electrodes and the absorbent layer for liquid absorption on the two sides of the flexible waterproof thin film of the electronic wetness-sensing absorbent article respectively, the flexible waterproof thin film, the flexible electrodes, and the liquid contained in the absorbent layer can form a variable electrolytic capacitor. The wetness state of the electronic wetness-sensing absorbent article can be obtained by only detecting the capacitance value of the capacitor and change thereof. In addition, by disposing the wetness sensing device in the electronic wetness-sensing absorbent article, for example, in a paper diaper, the wetness sensing device performs periodic charging and discharging operations on the wetness sensing lines in the paper diaper by using the charging and discharging unit, obtains voltage peak value data related to the variable capacitance value of the paper diaper, and forms a curve reflecting the wetness state of the paper diaper.

The curve contains various information such as that for determining whether urination has occurred, how long the wet state lasts, how long the urination lasts, how many times the urination occurs, the maximum degree of wetness and whether the paper diaper has been restored to the dry state, making the wetness detection more diversified and more informative. By using the absorbent article and related methods of the present application, the wetness state of the electronic wetness-sensing absorbent article can be dynamically, quickly, and accurately determined through analysis, providing a reliable basis for the use and replacement of disposable absorbent articles such as paper diapers and nappies.

BRIEF DESCRIPTION OF THE DRAWINGS

To describe the technical solutions of the embodiments of the present application or in the prior art more clearly, the drawings used in the description of the embodiments or prior art will be briefly introduced, obviously, the drawings in the following description are merely some embodiments of the present application, and those of ordinary skill in the art can obtain other drawings according to these drawings without an inventive effort.

DETAILED DESCRIPTION

The description of the following respective embodiments refers to the accompanying drawings, and is used for illustrating specific implementable embodiments. The directions and position terms, such as upper, lower, front, rear, left, right, inner, outer, top, bottom, side surface, etc., mentioned in the present application merely refer to directions or positions of the accompanying drawings. Therefore, the used directions and position terms are employed to describe and understand the present application rather than limit a protection scope of the present application.

Figure 1:
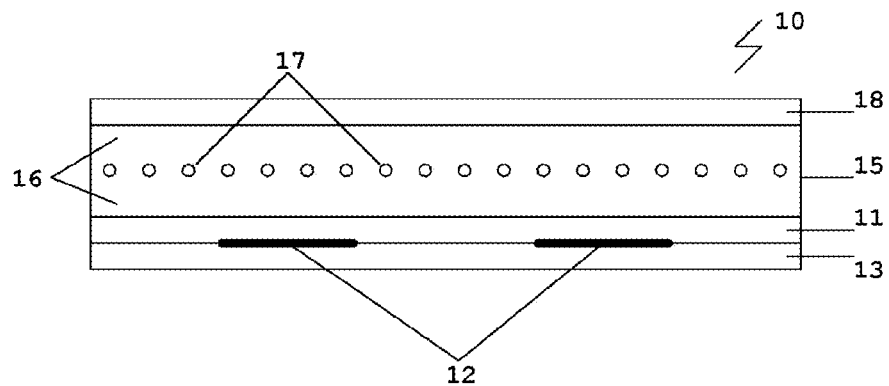
FIG. 1 is a schematic structural cross-sectional view of an electronic wetness-sensing absorbent article in the dry state according to an embodiment of the present application.

The present application is further described below with reference to the accompanying drawings. FIG. 1 is a schematic structural cross-sectional view of an electronic wetness-sensing absorbent article in the dry state according to an embodiment of the present application. The electronic wetness-sensing absorbent article 10 in FIG. 1 includes:

a flexible waterproof thin film 11;

at least two mutually separated and insulated flexible conductive electrodes 12 disposed on one surface of the flexible waterproof thin film 11;

a water-permeable braided fabric layer 18; and an absorbent layer 15 disposed on the other surface of the flexible waterproof thin film 11, located between the flexible waterproof thin film 11 and the water-permeable braided fabric layer 18, and adapted to absorb a liquid entering from the water-permeable braided fabric layer 18.

The flexible waterproof thin film 11, the flexible electrodes 12, and the liquid contained in the absorbent layer form a special (or generalized) non-polar variable electrolytic capacitor, in which the flexible electrodes 12 serve as two electrodes of the electrolytic capacitor, the flexible waterproof thin film 11 serves as a dielectric of the electrolytic capacitor, and the liquid, corresponding to the electrodes, in the absorbent layer serves as an electrolyte (electrolyte solution) of the electrolytic capacitor. The capacitance value of the electrolytic capacitor is related to the content and distribution of the liquid contained in the absorbent layer. The wetness state of the electronic wetness-sensing absorbent article 10 can be obtained by detecting the capacitance value of the electrolytic capacitor and analyzing the pattern of changes in the capacitance value.

Specifically, the electronic wetness-sensing absorbent article 10 generally refers to disposable paper diapers or paper nappies, and also applies to other disposable sanitary absorbent products such as paper urine pads, sanitary towels or the like. The flexible waterproof thin film 11 is generally made of a soft nontoxic polyethylene thin film (PE film). Commonly used PE films include gas-permeable films and gas-impermeable films. The gas-permeable films are commonly used for baby paper diapers while the gas-impermeable films are commonly used for adult paper diapers. At least two flexible electrodes 12 are disposed on one surface of the flexible waterproof thin film 11. The flexible electrodes are generally printed on the waterproof thin film using a carbon-based conductive ink, or may be formed by compositing a material such as an aluminum foil or a metal wire on the waterproof film. All these materials are flexible and do not affect the softness and use of the product. To avoid short circuit of the electrodes due to contact with human body or liquid, a flexible insulating protective layer 13 is provided to cover (or is composited on) the flexible electrodes 12. The insulating protective layer is generally made of nonwoven fabrics, hot air nonwoven fabrics, spunbonded fabrics, or the like.

The absorbent layer 15 on the other surface of the flexible waterproof thin film 11 includes a first absorbent 16 in close contact with the flexible waterproof thin film 11. The first absorbent 16 mainly includes powdery or flocculence cotton pulp, wood pulp, paper pulp or other materials, or may include tiny water storage spaces formed by a series of fibers or hairy braided fabrics. A second absorbent 17 is mixed in the first absorbent 16. The second absorbent 17 includes a tiny granular macromolecular water-absorbing resin (superabsorbent polymer, SAP) material. The water-permeable braided fabric layer 18 located above the absorbent layer 15 is generally made of materials with soft and water-permeable properties, such as, nonwoven fabrics, hot air nonwoven fabrics, or the like. The absorbent layer 15 is sandwiched between the flexible waterproof thin film 11 and the water-permeable braided fabric layer 18 and thereby fixed into shape.

Figure 2:
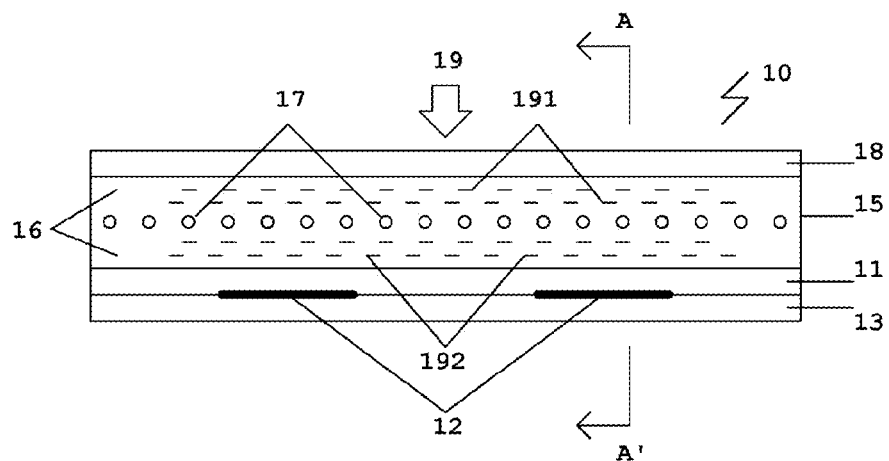
FIG. 2 is a schematic structural cross-sectional view of an electronic wetness-sensing absorbent article in the wet state according to an embodiment of the present application.

Referring to FIG. 2, FIG. 2 is a schematic structural cross-sectional view of an electronic wetness-sensing absorbent article in the wet state according to an embodiment of the present application. In FIG. 2, 19 denotes a liquid (including water, urine, sweat or other secretions and excrements of a human body or an animal) applied to the electronic wetness-sensing absorbent article 10. The liquid 19 enters the absorbent layer 15 of the electronic wetness-sensing absorbent article 10 through the water-permeable braided fabric layer 18, and is first absorbed by the first absorbent 16 of the absorbent layer 15. If there is a small amount of liquid, the liquid is absorbed only by the upper layer of the first absorbent 16 (in this case, the liquid 19 is denoted by 191). If there is a large amount of liquid, the liquid soon reaches the lower layer of the first absorbent 16 (in this case, the liquid 19 is denoted by 192). The flexible waterproof thin film 11 is located below the liquid 192. Due to the barrier of the flexible waterproof thin film 11, it stops the liquid 192 from leaking downwards. Since the liquid 192 is in close contact with the flexible electrodes 12, the liquid 192, the flexible electrodes 12, and the flexible waterproof thin film 11 can jointly form a generalized special non-polar variable electrolytic capacitor, in which the flexible electrodes 12 serve as two electrodes of the electrolytic capacitor, the flexible waterproof thin film 11 serves as an insulating dielectric of the electrolytic capacitor, and the liquid 192 (for example, urine containing salts) as an electrolyte solution of the electrolytic capacitor. The capacitance value of the variable electrolytic capacitor is related to the liquid content of the first absorbent 16, and is also directly related to the wet area and liquid distribution, corresponding to the flexible electrodes 12, of the first absorbent on the flexible waterproof thin film 11. By monitoring the capacitance value between the flexible electrodes 12, the liquid content or coverage (or distribution) information of the liquid contained in the first absorbent 16 can be obtained, which is described in further detail below with reference to the accompanying drawings.

Figure 3:
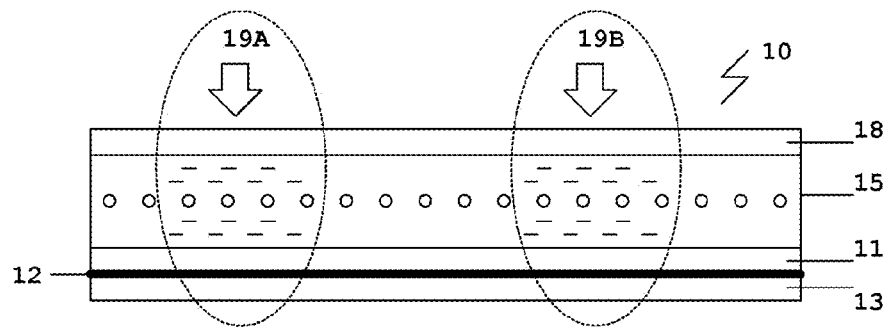
FIG. 3 is a schematic cross-sectional view taken along an A-A' direction in FIG. 2.

Referring to FIG. 3, FIG. 3 is a schematic cross-sectional view taken along an A-A' direction in FIG. 2. Different from FIG. 2, two wet regions can be seen in FIG. 3, namely, 19A and 19B. Assuming that the capacitance value generated by 19A is C19$a$ and the capacitance value generated by 19B is C19$b$, the overall capacitance value presented by the electronic wetness-sensing absorbent article 10 is C19$a$+C19$b$. That is, the capacitance value of the variable electrolytic capacitor is in direct proportion to the number of wet regions and the size of the wet area.

Figure 4:
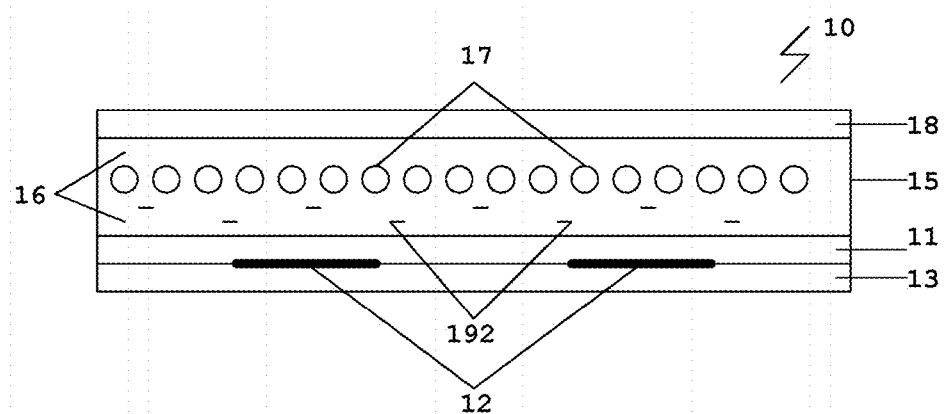
FIG. 4 is a schematic structural cross-sectional view of an electronic wetness-sensing absorbent article restored to the dry state according to an embodiment of the present application.

Referring to FIG. 4, FIG. 4 is a schematic structural cross-sectional view of an electronic wetness-sensing absorbent article restored to the dry state according to an embodiment of the present application. In the absorbent layer 15, the absorption rate of the first absorbent 16 is faster than that of the second absorbent 17, and the liquid (for example, urine) entering from the water-permeable braided fabric layer 18 is first absorbed by the first absorbent 16. The second absorbent (SAP) 17 contained in the first absorbent 16, though having a slower absorption rate than that of the first absorbent 16, has a stronger liquid absorption capacity than that of the first absorbent 16, and can absorb water of a volume that is hundreds or even thousands times the volume of the second absorbent and trap the water in the macromolecular water-absorbing resin (SAP). Due to the presence of the SAP, the water contained in the first absorbent 16 is gradually transferred into the second absorbent 17 and trapped therein, such that the amount of water in the first absorbent 16 is reduced. FIG. 4 shows that the water 191 in the upper layer of the absorbent layer 15 has been absorbed by the second absorbent 17, and the amount of water 192 in the lower layer of the absorbent layer 15 is greatly reduced, because the original tiny granular SAP expands after absorbing the water. The electronic wetness-sensing absorbent article 10 as a whole exhibits a dry state under the action of the SAP. In this case, it may be considered that the electronic wetness-sensing absorbent article 10 has been restored to the dry state. Meanwhile, the capacitance value of the electrolytic capacitor presented between the flexible electrodes 12 of the electronic wetness-sensing absorbent article 10 decreases significantly compared with FIG. 2.

The first absorbent 16 may be made of an absorbent material having tiny water storage spaces that is made of a particular material/fiber, such as hot air nonwoven fabrics, fluffy fabrics, and short fibers. The tiny spaces have certain water storage capacities, and therefore can absorb water/liquid. In an embodiment, the tiny granular macromolecular water-absorbing resin may be distributed in the tiny water storage spaces to reabsorb the water in the spaces, such that the water storage spaces can change from the wet state back to the dry state.

Figure 5:
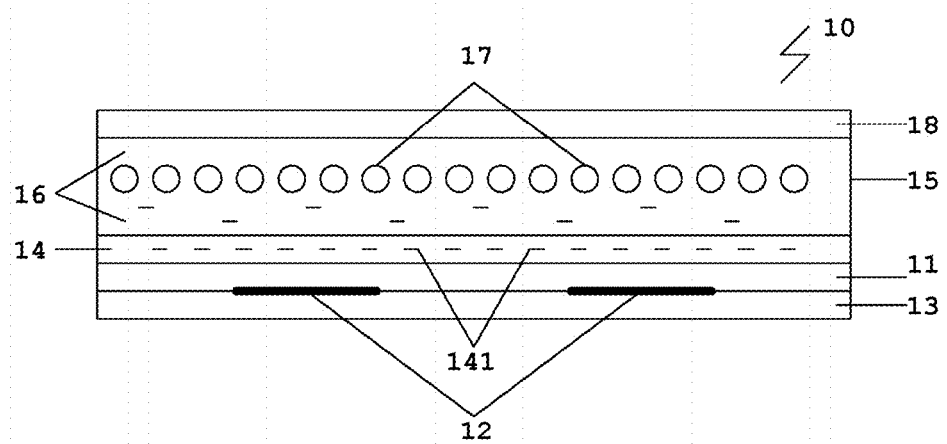
FIG. 5 is a schematic structural diagram of an electronic wetness-sensing absorbent article including a hydrophilic layer according to an embodiment of the present application.

Referring to FIG. 5, FIG. 5 is a schematic structural diagram of an electronic wetness-sensing absorbent article including a hydrophilic layer according to an embodiment of the present application. In some application occasions, the absorbent article may be expected to have a wetness state memory effect, i.e., it is expected that the wet state or wetness degree can memorized regardless of whether a wet place has changed to the dry state. In this case, this function can be realized by adding a hydrophilic layer between the flexible waterproof thin film 11 and the first absorbent 16. 14 in FIG. 5 denotes the hydrophilic layer, which has strong liquid absorption and preserving capacities, and is adapted to absorb the liquid from the absorbent layer 15 and preserve the liquid, such that the surface area of the flexible electrodes 12 covered by the liquid remains unchanged, and accordingly the capacitance value of the electrolytic capacitor remains substantially unchanged. It can be seen from FIG. 5 that although the amount of water contained in the first absorbent 16 above the hydrophilic layer 14 is reduced, the amount water 141 contained in the hydrophilic layer 14 remains substantially unchanged, such that the capacitance value of the electrolytic capacitor presented between the flexible electrodes 12 remains substantially unchanged. In other words, it may be considered that the hydrophilic layer 14 can enhance the wetness memory effect, i.e., can reduce the change of the capacitance value of the variable electrolytic capacitor from large to small.

On the contrary, if the wetness memory effect needs to be reduced or the change of the capacitance value of the variable electrolytic capacitor from large to small needs to be enhanced so as to detect whether the electronic wetness-sensing absorbent article 10 has been restored to the dry state, a hydrophobic layer (denoted by the same reference sign 14 in the figure) may be added between the flexible waterproof thin film 11 and the first absorbent 16. The hydrophilic layer and the hydrophobic layer having different properties have impact on the accumulation of the water in the first absorbent 16 on the surface of the flexible waterproof thin film 11, and therefore have impact on the change of the capacitance value of the variable electrolytic capacitor, leading to different patterns of capacitance change. Therefore, different parameter properties can be provided to adapt to different detection functions and purposes. For the electronic wetness-sensing absorbent article with the hydrophobic layer, if the liquid entering from the water-permeable braided fabric layer 18 is injected at a high speed, the liquid can directly reach the hydrophobic layer 14 to wet the hydrophobic layer. Since the hydrophobic layer is in close contact with the flexible waterproof thin film and is opposite to the flexible electrodes, and wetting the hydrophobic layer will increase the capacitance value of the electrolytic capacitor, it can be determined whether there is a large amount of liquid entering the absorbent article by detecting the capacitance value. Since the water trapping capacity of the hydrophobic layer is relatively poor, the water moisturizing the hydrophobic layer is gradually absorbed by the absorbent layer once the absorbent layer 15 (in particular the second absorbent 17 in the absorbent layer 15) begins to absorb water, such that the amount of water in the hydrophobic layer is reduced, and accordingly the capacitance value of the electrolytic capacitor decreases.

In general, due to the presence of the hydrophobic layer 14, the effect of the capacitance value of the electrolytic capacitor changing from small to large and then from large to small is amplified, which corresponds to the process that the electronic wetness-sensing absorbent article 10 changes from dry to wet and then from wet to dry. However, if the total amount of liquid entering the absorbent layer 15 is so large that exceeds the absorption capacity of the absorbent layer 15, and saturates the absorbent layer, the liquid will be accumulated on the hydrophobic layer. In this case, the capacitance value of the electrolytic capacitor increases and can no longer reduce. Therefore, it can be determined through analysis whether the absorbent layer has entered a saturated state. For the electronic wetness-sensing absorbent layer 10 with the hydrophilic layer 14, its pattern of capacitance change is close to one-way increase since it is easy for the electronic wetness-sensing absorbent layer 10 with the hydrophilic layer 14 to change from dry to wet but difficult to change from wet to dry. Correspondingly, the change of the capacitance value from small to large is relatively obvious, and the change of the capacitance value from large to small is not obvious. Therefore, the pattern of capacitance change can be regulated by selectively disposing the hydrophilic layer or hydrophobic layer. In an actual application, the hydrophilic layer includes any one or any combination of a hydrophilic material layer, a hydrophilic thin film, hydrophilic fibers, or a hydrophilic coating, for example, toilet paper with better water absorption performance, cotton or other hydrophilic fibers/coatings. The hydrophobic layer includes nonwoven fabrics or other hydrophobic fibers, thin film and coating, and so on.

Because the flexible waterproof thin film 11 is hydrophobic, it is hard for water to accumulate on the surface of the flexible waterproof thin film 11. In order to strengthen the water accumulation ability between the flexible waterproof thin film 11 and the hydrophilic layer 14, surfactant can be printed or sprayed on the surface of the flexible waterproof thin film 11. The molecular structure of the surfactant is amphiphilic, i.e. one end of the surfactant includes a hydrophilic group, and the other end includes a hydrophobic group. As a result of the presence of these groups, the flexible waterproof thin film 11 becomes less repellent, and water molecules can be adsorbed on the surface of the flexible waterproof thin film 11 without rejection. One type of suitable surfactant is anionic surfactant. Commonly used anionic surfactants include alkyl sulfonate, fatty alcohol ether sodium sulfate, and so on. In practice, directly spraying the surfactant on the surface of the hydrophilic layer 14 can achieve the same effect.

Figure 6:
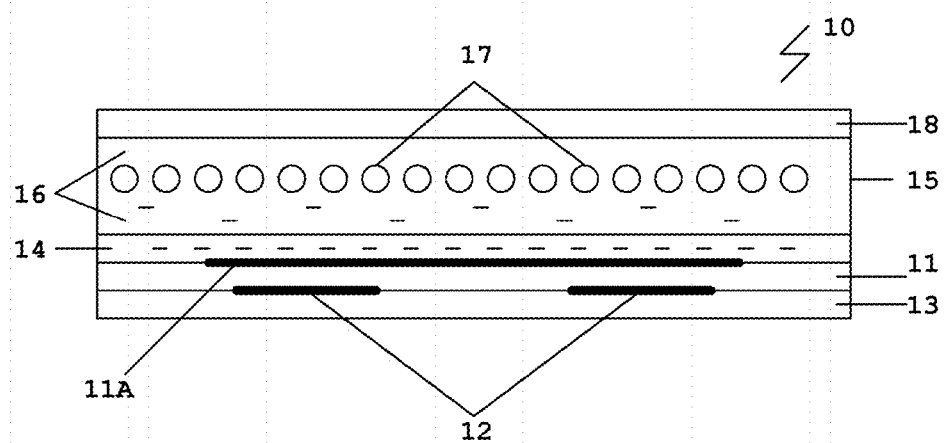
FIG. 6 is a schematic structural diagram of an electronic wetness-sensing absorbent article including an anti-permeation coating according to an embodiment of the present application.

Referring to FIG. 6, FIG. 6 is a schematic structural diagram of an electronic wetness-sensing absorbent article including an anti-permeation coating according to an embodiment of the present application. In an actual application, the flexible waterproof thin film 11 is gas-permeable. Especially for a baby paper diaper absorbent article, a waterproof gas-permeable polyethylene thin film (PE film) is generally used as the waterproof thin film. Such a thin film is waterproof and gas-permeable, and is more conformable to wear. Although the liquid cannot flow from the gas-permeable flexible waterproof thin film 11, the permeated vapor may short-circuit the flexible electrodes 12 printed on the flexible waterproof thin film 11, which influences the capacitance value between the two electrodes. To avoid short circuit of the flexible electrodes 12 due to liquid leakage, in FIG. 6, the other surface of the flexible waterproof thin film 11 corresponding to the electrodes 12 includes an anti-permeation coating 11A. The anti-permeation coating can be printed at the corresponding position using a waterproof ink and can stop the vapor on the hydrophilic layer 14 from penetrating through the flexible waterproof thin film 11 to short-circuit the flexible electrodes 12. The waterproof ink includes an intaglio surface printing ink, and the ink may contain some waterproof agents, for example, a fluorocarbon resin, a fluorocarbon polymer, an acrylic acid waterproof coating, a polyurethane waterproof coating, etc., so as to achieve a better waterproof effect.

Figure 7:
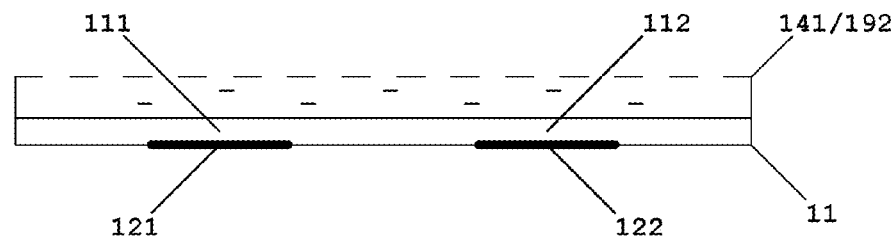
FIG. 7 is a schematic structural diagram of the key part that influences the capacitance value of a variable electrolytic capacitor of an electronic wetness-sensing absorbent article according to an embodiment of the present application.

Further, referring to FIG. 7, FIG. 7 is a schematic structural diagram of the key part that influences the capacitance value of a capacitor of an electronic wetness-sensing absorbent article according to an embodiment of the present application. In FIGS. 7, 121 and 122 denote two electrodes separately on the left and the right (both belonging to the electrodes 12), 111 and 112 denote flexible waterproof thin films in close contact with the electrodes 121 and 122, 141/192 denotes the liquid in close contact with the flexible waterproof thin film 11 and close to the electrodes 121 and 122. These three parts form the foregoing generalized non-polar variable electrolytic capacitor, in which 121 and 122 form the electrodes of the electrolytic capacitor, the flexible waterproof thin films 111 and 112 form insulating dielectrics of the electrolytic capacitor, and 141/192 (for example, urine containing salts) serves as an electrolyte/electrolyte solution of the electrolytic capacitor. The capacitance value of the variable electrolytic capacitor is related to the contact area between the liquid 141/192 and the flexible waterproof thin film 111/112. The content/coverage area information of the liquid contained in the first absorbent 16, particularly in the hydrophilic layer/hydrophobic layer 14, can be obtained by monitoring the capacitance value between the flexible electrodes 12. The liquid change condition in the first absorbent 16 can be dynamically reflected by the capacitance value change of the variable electrolytic capacitor. A quantified wetness state can be obtained by detecting the capacitance value of the electrolytic capacitor.

Figure 8:
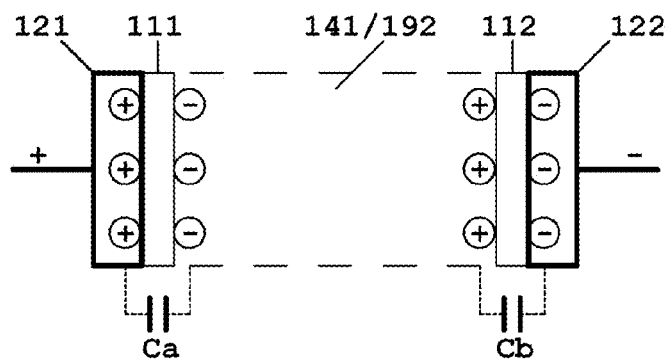
FIG. 8 is an equivalent schematic structural diagram of a variable electrolytic capacitor of an electronic wetness-sensing absorbent article according to an embodiment of the present application.

Further, referring to FIG. 8, FIG. 8 is an equivalent schematic structural diagram of a variable electrolytic capacitor of an electronic wetness-sensing absorbent article according to an embodiment of the present application. In FIGS. 8, 121 and 122 denote an anode and a cathode formed by the flexible electrodes 12 of the variable electrolytic capacitor. 111 and 112 are dielectrics attached to the flexible electrodes 121 and 122 and formed by the flexible waterproof thin film 11 (equivalent to a metal oxide thin film of a conventional electrolytic capacitor). 141 and 192 denote electrolyte solutions (for example, urine containing salts) covering the flexible waterproof thin films 121 and 122. If a positive voltage is applied to the flexible electrode 121 and a negative voltage is applied to the flexible electrode 122, positive and negative charges are respectively generated on 121 and 122, ions of opposite polarities in the electrolyte 141/192 are attracted by these positive and negative charges to be accumulated on the other surface of the flexible waterproof thin film 111/112, such that a capacitance effect similar to that of the conventional electrolytic capacitor is generated, and two equivalent serial-connected electrolytic capacitors Ca and Cb are formed. In Ca, the flexible electrode 121 is the anode, and the electrolyte 141/192 is the cathode, same as the conventional electrolytic capacitor. In Cb, the electrolyte 141/192 is the anode, and the flexible electrode 122 is the cathode, different from the case in which the electrolyte solution is a cathode of the conventional electrolytic capacitor. However, on the contrary, if a positive voltage is applied to the flexible electrode 122 and a negative voltage is applied to the flexible electrode 121, the case is reversed, that is, the case of the Cb is same as that of the conventional electrolytic capacitor and the case of the Ca is different from that of the conventional electrolytic capacitor to some extent.

The key of the electrolytic capacitor is that the electrolyte/electrolyte solution is used as the electrodes of the capacitor. The electrolyte solution in the conventional electrolytic capacitor serves as the cathode. This is because that the metal oxide film serving as the dielectric has unilateral conductivity, and severe electric leakage is caused if the voltage is applied reversely. If the dielectric has no unilateral conductivity, the electrolyte solution may serve as either the cathode or the anode of the capacitor, thus the electrolytic capacitor is non-polar. The variable electrolytic capacitor of the embodiment of the present application is one of such cases, in no electric leakage will occur regardless of whether a positive voltage or a negative voltage is applied, and the capacitance value is the same. The variable electrolytic capacitor in the embodiments of the present application can be considered as an improvement on and a supplement to the conventional electrolytic capacitor. Therefore, the variable electrolytic capacitor of the present application can be referred to as a generalized special electrolytic capacitor.

Figure 9:
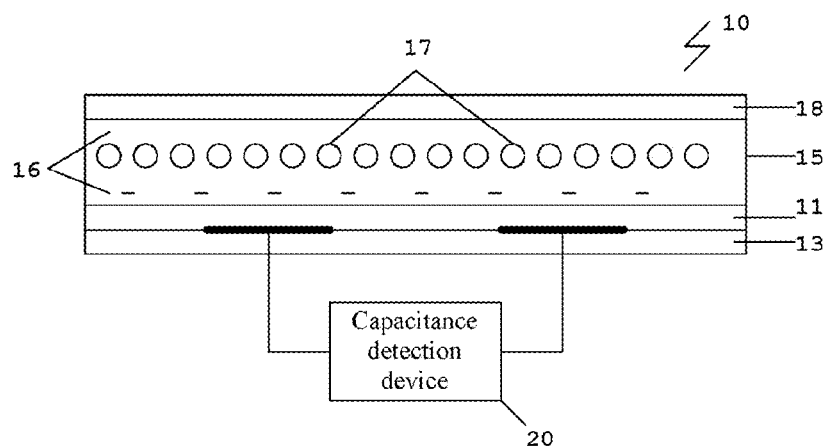
FIG. 9 is a schematic structural diagram of performing capacitance detection on an electronic wetness-sensing absorbent article according to an embodiment of the present application.

Referring to FIG. 9, FIG. 9 is a schematic structural diagram of performing capacitance detection on an electronic wetness-sensing absorbent article according to an embodiment of the present application. To monitor the usage status, the liquid absorption status and the absorption capacity change of the electronic wetness-sensing absorbent article 10, in FIG. 9, a capacitance detection device 20 is included. The capacitance detection device is connected to two flexible electrodes 12 of the electronic wetness-sensing absorbent article 10, can monitor the change of the capacitance value between the flexible electrodes 12 in real time, and can learn from the change of the capacitance value a process that the liquid enters from the water-permeable braided fabric layer 18, being absorbed by the first absorbent 16, then being absorbed and trapped by the second absorbent 17, such that the electronic wetness-sensing absorbent article 10 changes from dry to wet and then changes from wet to dry. For the electronic wetness-sensing absorbent article with the hydrophilic layer having the wetness memory effect, the capacitance detection device is mainly adapted to monitor whether the absorbent article is in the wet state, the wetness degree/area/range and so on, but usually cannot reflect whether the absorbent article has been restored to the relatively dry state.

Figure 10:
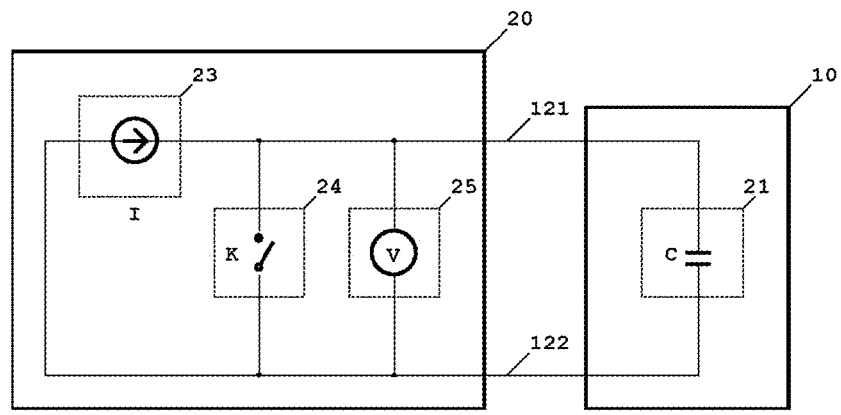
FIG. 10 is a schematic diagram of a capacitance detection circuit of an electronic wetness-sensing absorbent article according to an embodiment of the present application.

Further, referring to FIG. 10, FIG. 10 is a schematic diagram of a capacitance detection circuit of an electronic wetness-sensing absorbent article according to an embodiment of the present application. In FIG. 10, the capacitance detection device 20 is connected to the electronic wetness-sensing absorbent article 10 through the flexible electrodes 121 and 122. The electronic wetness-sensing absorbent article 10 includes a variable capacitor 21 (C, which is an equivalent capacitor of the foregoing serial-connected Ca and Cb), and the capacitor C mainly includes the flexible electrodes 12, the flexible waterproof thin film 11 and the liquid (electrolyte solution) contained in the first absorbent 16 or the hydrophilic thin film 14. The more the liquid contained in the first absorbent 16 or the hydrophilic thin film 14 is, the larger the area of the liquid corresponding to the flexible electrodes is, and the larger the presented capacitance value of the electrolytic capacitor is. By detecting the capacitor C and analyzing the change of the capacitance value thereof, the wet condition of the electronic wetness-sensing absorbent article 10 and whether the absorption capacity thereof has approached to saturation can be determined.

The capacitance detection device 20 includes a charging unit 23 (current source I), a discharging unit 24 (electronic switch K) and a voltage detection unit 25, and the above three units can perform periodic charging and discharging and voltage measurement operations on the capacitor C of the electronic wetness-sensing absorbent article 10 through the flexible electrodes 12 (including 121 and 122), such that the detection on the capacitance value of the capacitor C is realized. Assuming that charging current is I, charging time is T, and the voltage between two ends of the capacitor C before charging is 0, the calculation formula is as follows:

$$C = Q/V = I \times T/V, \text{ i.e., } V = I \times T/C$$

From the above formula, it can be seen that in the charging process, the voltage between two ends of each flexible electrode 12 is increased with time, when the time reaches T (charging ending time), the voltage value is maximum (V), the voltage V is referred to as a peak voltage of one charging period. The value of the peak voltage V is inversely proportional to the capacitance value C of the electronic wetness-sensing absorbent article 10. The more the liquid (electrolyte solution) 141/192 in the electronic wetness-sensing absorbent article 10 is, the larger the wet area is, the larger the capacitance value of the capacitor C is, and the lower the voltage value V obtained through the calculation formula V=I×T/C is. Therefore, by detecting the voltage V, the capacitance value C is known, and the wetness degree/the wet area of the electronic wetness-sensing absorbent article 10 can further be determined.

After the charging to V and reading the value of V, the discharging unit 24 (K) in the circuit is switched on, the electrodes 121 and 122 are short-circuited. The capacitor C discharges through the electronic switch K till the voltage becomes 0, then K is switched off again at the beginning of the next charging period, the charging unit 23 charges again, thereby obtaining the next charging peak value voltage V. By the periodic charging and discharging operations, a series of peak value voltage V data information changing with the time can be obtained. In an actual application, charging and discharging operations can be performed once per second, i.e., the capacitance value of the absorbent article 10 presented between the electrodes 12 is detected once per second, therefore, the monitoring on the wet condition of the absorbent article is realized per second.

The capacitance detection in FIG. 10 implemented in a direct current charging and discharging manner in is a common means, but in an actual application, there are many ways of detecting capacitance, including applying an alternating voltage or an alternating current to two ends of the electrodes to obtain the capacitance value. FIG. 10 can be regarded as an illustration of one way of capacitance detection rather than a limitation to the capacitance detection of the present application.

Figure 11A:
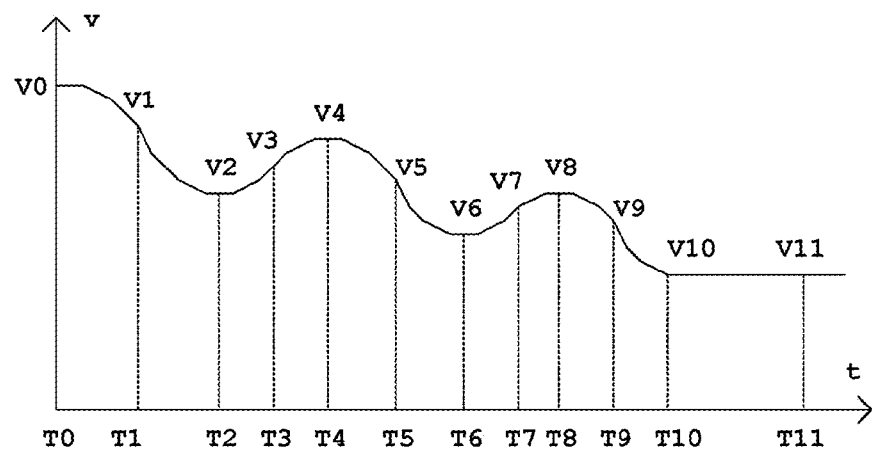
FIG. 11A is a diagram of a voltage curve related to the capacitance value of an electronic wetness-sensing absorbent article according to an embodiment of the present application.

Further, referring to FIG. 11A, FIG. 11A is a diagram of a voltage curve showing a voltage in inverse proportion to the capacitance value of an electronic wetness-sensing absorbent article according to an embodiment of the present application. In FIG. 11A, the horizontal axis of the coordinate system is time t, the vertical axis is voltage v, and the coordinate system is constituted by a series of voltage peak value V generated by the periodic charging and discharging in FIG. 10. Assume that the electronic wetness-sensing absorbent article 10 is a paper diaper, the peak value voltage in an original state (T0) is V0 and corresponds to an original dry state, the voltage value is the highest in the whole curve and represents that the corresponding capacitance value C of the paper diaper is the smallest (the capacitance value of the electrolyte is basically 0, and two ends of the flexible electrodes 12 present a relatively small dielectric capacitance value in the absence of electrolyte solution. To prevent V0 from being excessively high, a known capacitor may be added between the two electrodes of the capacitance detection circuit to reduce V0). When a wetness state occurs (for example, during urination), an electrolytic capacitor effect occurs. The capacitance of the capacitor C begins to increase, and the corresponding voltage value V begins to decrease. By taking the original value V0 as a reference point, when the voltage at certain time point (T1) is reduced to a certain value (V1, for example, assuming that V1 is 70%-97% of V0, i.e., the voltage is reduced by 3%-30% from the original value V0), the electronic wetness-sensing absorbent article 10 can be considered as wet, or the wetness state of the electronic wetness-sensing absorbent article 10 is determined.

Urination is firstly reflected by an increase in the content of urine in the first absorbent 16. When urination stops, the water in the first absorbent 16 is gradually transferred into the SAP due to the high water absorption capacity of the second absorbent 17 (SAP) and is effectively trapped, such that the water in the first absorbent 16 is reduced, the corresponding capacitance value C is reduced, finally, the periodic charging and discharging peak value voltage V generated between two ends of the flexible electrodes 12 of the capacitance detection device 20 is increased, and a valley is formed in the curve. Assuming the voltage at a time point T2 is a valley value V2, a voltage value at a time point T3 is V3, and V3 is greater than V2 (for example, V3 is greater than V2 by 3%-30%, i.e., V3 is 103%-130% of V2), at this time, urination is considered stopped at the valley time point T2 and, at the time point T3, the electronic wetness-sensing absorbent article 10 has been restored to a relatively dry state, or the absorption capacity of the second absorbent 17 has not reached the saturated state and has the capacity of absorbing more water later.

As time goes on, the water in the first absorbent 16 is further reduced, and the curve continues to rise after T3 and reaches another peak value V4 at a time point T4. The peak value V4 is less than the original peak value V0 since the electronic wetness-sensing absorbent article was once wetted and cannot be restored to the original dry state. If a user urinates in this case, the curve will drop again. When dropping to a time point T5, the voltage value V5 is reduced by 3%-30% compared with the peak value V4 (i.e., V5 is 70%-97% of V4). It can be considered that the electronic wetness-sensing absorbent article 10 is wet again, i.e., a new wet condition is determined again. The process is repeated: another valley is reached at T6/V6, the electronic wetness-sensing absorbent article 10 has been restored to the dry state at T7/V7, another peak is reached at T8/V8, another occurrence of urination is determined at T9/V9, and a valley is reached at T10/V10. Different from the above, after T10, the curve does not rise any more, which means that the second absorbent 17 has been saturated, and the electronic wetness-sensing absorbent article 10 needs to be replaced.

In an actual application, whether the electronic wetness-sensing absorbent article needs to be replaced has many different determining standards representing different wetness states. The curve contains various pieces of information for determining, specifically including whether urination has occurred, how long the urination lasts, how long the urination (liquid excretion) takes, how many times urination occurs, the maximum degree of wetness, whether dryness has been restored, whether the liquid absorbent has reached a saturation state, etc., and the specific content is further described in the following drawings.

Figure 11B:
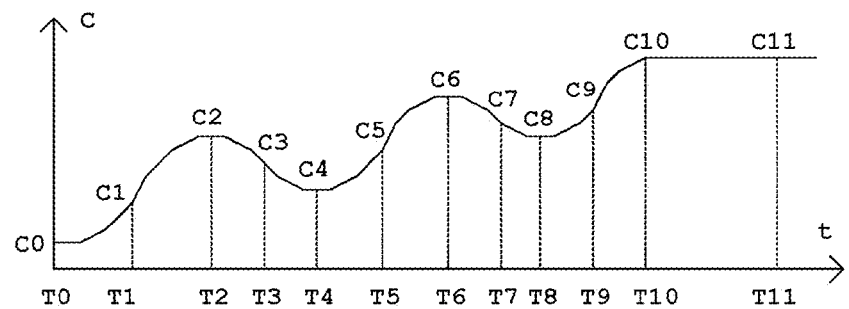
FIG. 11B is a diagram of a capacitance curve related to a wetness degree of an electronic wetness-sensing absorbent article according to an embodiment of the present application.

Further, referring to FIG. 11B, FIG. 11B is a diagram of a capacitance curve related to a wetness degree of an electronic wetness-sensing absorbent article according to an embodiment of the present application, and the curve corresponds to FIG. 10 but having a reversed changing pattern. In FIG. 11B, the horizontal axis of the coordinate system is time t, the vertical axis is capacitance value C, and the coordinate system is constituted by a series of capacitance value data related to the wetness degree of the electronic wetness-sensing absorbent article obtained by periodic charging and discharging (or by other manners) of FIG. 10. Assume that the electronic wetness-sensing absorbent article 10 is a paper diaper, an original capacitance value C0 at an original state (T0) corresponds to an original dry state, and the capacitance value is the smallest in the whole curve. When wetness state occurs (for example, during urination), an electrolytic capacitance effect occurs, and the capacitance value of capacitor C is increased. By taking the original value C0 as a reference point, when the capacitor rises to a certain value (for example, C1) at a certain time point (T1), the electronic wetness-sensing absorbent article 10 can be considered as wet, or it is determined that the electronic wetness-sensing absorbent article 10 is in the wet state.

Urination is firstly reflected by an increase in the content of urine in the first absorbent 16. When urination stops, the water in the first absorbent 16 is gradually transferred into the SAP due to the high water absorption capacity of the second absorbent 17 (SAP) and is trapped, such that the water in the first absorbent 16 is reduced, the corresponding capacitance value C is reduced, and a peak is formed in the curve. Assuming that the capacitance at a time point T2 is a peak value C2, a capacitance value at a time point T3 is C3, and C3 is less than C2 by a certain degree, at this time, the urination is considered stopped at the peak time point T2 and, at the time point T3, the electronic wetness-sensing absorbent article 10 has been restored to a relatively dry state, or the absorption capacity of the second absorbent 17 has not reached the saturated state and has the capacity of absorbing more water later.

As time goes on, the water in the first absorbent 16 is further reduced. The curve continues to drop after T3 and reaches another valley value C4 at a time point T4, and the valley capacitance value C4 is greater than the original peak value C0 since the electronic wetness-sensing absorbent article was once wet and cannot be restored to the original dry state. If a user urinates in this case, the curve will rise again. When rising to a time point T5, the capacitance value C5 is increased by a certain degree compared with the valley value C4, it can be considered that the electronic wetness-sensing absorbent article 10 is wet again, i.e., a new wet condition is determined. The process is repeated: a peak is reached at T6/V6, the electronic wetness-sensing absorbent article 10 has been restored to the dry state at T7/V7, another valley is reached at T8/V8, another occurrence of urination is determined at T9/V9, and a valley is reached at T10/V10. Different from the above, after T10, the curve does not drop any more, which means that the second absorbent 17 has been saturated, and the electronic wetness-sensing absorbent article 10 needs to be replaced.

In an actual application, whether the electronic wetness-sensing absorbent article needs to be replaced has many different determining standards representing different wetness states. The curve contains various pieces of information for determining, specifically including whether urination has occurred, how long the urination lasts, how long the urination (liquid excretion) takes, how many times urination occurs, the maximum degree of wetness, whether dryness has been restored, whether the liquid absorbent has reached a saturation state, etc., and the specific content is further described in the following drawings.

Figure 12:
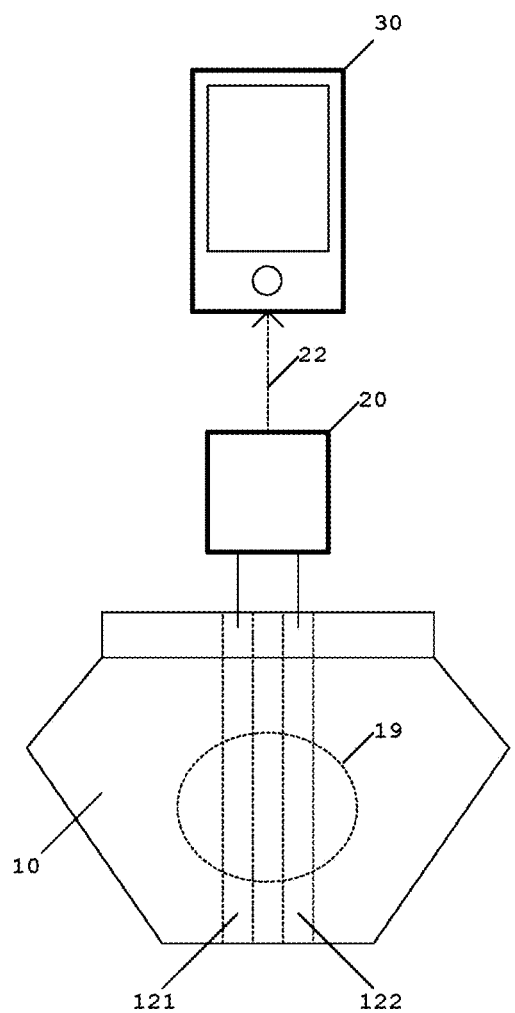
FIG. 12 is a schematic diagram of devices in a system for implementing wetness detection, data sending and receiving and state displaying on an electronic wetness sensing paper diaper according to an embodiment of the present application.

Further, referring to FIG. 12, FIG. 12 is a schematic diagram of devices in a system for implementing wetness detection, data sending and receiving and state displaying on a disposable variable capacitor type electronic wetness sensing paper diaper according to an embodiment of the present application. The absorbent article 10 in FIG. 12 is a disposable paper diaper. The paper diaper 10 includes two wetness sensing lines (sensing line electrodes) 121 and 122, which can sense a wetness state of the paper diaper 10, and 19 denotes a wet range/region of the paper diaper 10. The wetness sensing lines are connected to the capacitance detection device 20, which can also be referred to as a wetness detection device, a urination sensor or a sensor device. The wetness detection device 20 includes a wireless transmitter/unit (low power wireless, Bluetooth transceiver, Wi-Fi transceiver, etc.), and can send an urination-related data signal to a smart phone 30 (or a wireless receiver and state indicator) through a wireless signal 22. The phone processes the data signal, extracts urination information in the data, including information i.e., whether urination has occurred, how long the wetness state lasts, how long the urination takes, how many times the urination occurs, the maximum degree of wetness and whether dryness has been restored, whether the absorbent layer/the absorbent has reached a saturated state, displays related information on the phone (or the wireless receiver and state indicator) and sends a signal indicating that the paper diaper/absorbent article needs to be replaced at proper time.

Figure 13:
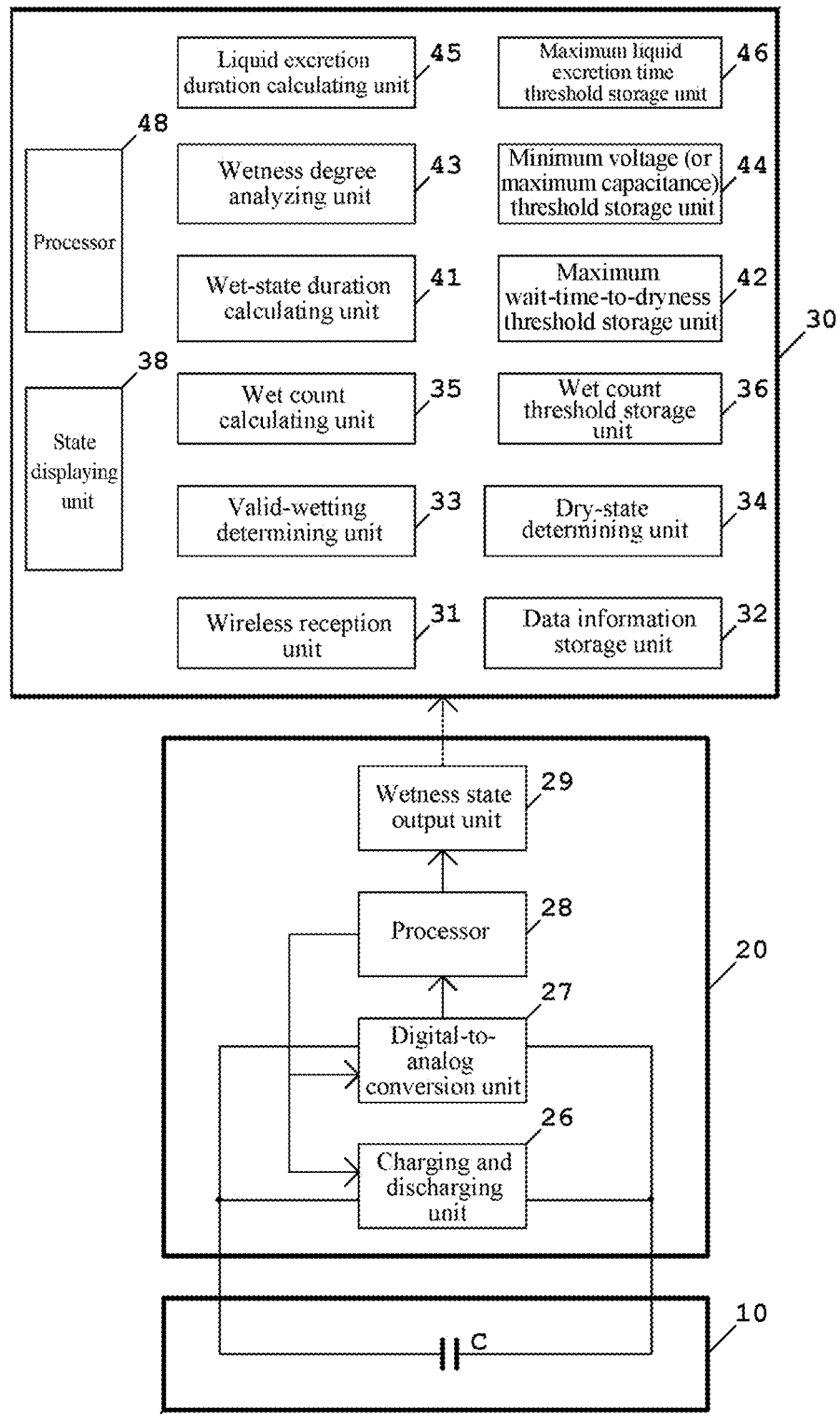
FIG. 13 is a block diagram of a functional structure of a wetness sensing device according to an embodiment of the present application.

Further, referring to FIG. 13, FIG. 13 is a block diagram of a functional structure of a wetness detection device according to an embodiment of the present application. FIG. 13 includes an electronic wetness-sensing absorbent article 10 (for example, an electronic wetness sensing paper diaper). The electronic wetness-sensing absorbent article 10 mainly includes a variable capacitor C mainly constituted by flexible electrodes 12, a flexible waterproof thin film 11 and liquid in a first absorbent 16 or hydrophilic layer 14 (electrolyte). The variable capacitor C is connected to a wetness detection device 20 through the flexible electrodes 12, the wetness detection device 20 includes a charging and discharging unit 26, a digital-to-analog conversion unit 27 and a processor 28, where the processor 28 controls the charging and discharging unit 26 to realize periodic charging and discharging operations on the capacitor C, and obtains voltage peak data generated by charging through the digital-to-analog conversion unit 27 (or calculates the capacitance value accordingly). Further, the wetness detection device 20 also includes a wetness state output unit 29, which can output data information related to the wetness state of the electronic wetness-sensing absorbent article 10 by means such as low power wireless, Bluetooth, Wi-Fi, or the like, and can also output data information locally in a sound-light alarm.

The wireless signal sent by the wetness state output unit 29 is received by a wireless reception unit 31 in the wireless receiver and state indicator 30, and related data is stored into a data information storage unit 32. The series of data information can generate a voltage curve (or capacitance curve) related to the wetness state of the electronic wetness-sensing absorbent article 10.

To determine through analysis the curve to obtain related state information, FIG. 13 further includes a valid-wetting determining unit 33 and a dry-state determining unit 34. The valid-wetting determining unit 33 includes a preset wetness determining voltage (or capacitance) threshold. When the voltage curve drops to a preset threshold (for example, dropping by 3%-30%) from an original value or a certain peak value (or the capacitance curve rises from an original value or a valley value to a preset threshold), it is determined that the absorbent article 10 is wet, or wetting occurs once. The dry-state determining unit 34 includes a preset dry restoration voltage (or capacitance) threshold. When the curve reaches a preset threshold, the dry state of the electronic wetness-sensing absorbent article can be determined.

Further, the wireless receiver and state indicator 30 may further include a wet count calculating unit 35 and a wet count threshold storage unit 36, which can calculate the number of times of occurrence of urination of the electronic wetness-sensing absorbent article (the number of times of urination, for example, it can be determined that three times of urination occur at T1, T5 and T9 in the curve in each of FIG. 11A and FIG. 11B). When the number of times of wetting reaches a preset threshold (for example, 1-10 times), a signal indicating that the absorbent article 10 needs to be replaced is sent by a state displaying unit 38.

Further, the wireless receiver and state indicator 30 may further include a wet-state duration calculating unit 41 and a maximum wait-time-to-dryness threshold storage unit 42. If the electronic wetness-sensing absorbent article 10 has not been restored to the dry state from the moment when one time of occurrence of a wetness state is determined (for example, T9 in FIG. 11A) to a certain preset time threshold (i.e., the maximum wait-time-to-dryness threshold, for example, 1-60 min, and from T9 to T11 in FIG. 11A), it can be considered that the electronic wetness-sensing absorbent article 10 has reached a saturated state and the signal indicating that the absorbent article 10 needs to be replaced can be sent by the state displaying unit 38.

Further, the wireless receiver and state indicator 30 may further include a wetness degree analyzing unit 43 and a minimum voltage (or maximum capacitance) threshold storage unit 44. When the voltage curve drops to the minimum voltage threshold (for example, 10%-90% of the original value; for example, V10 in FIG. 11A) from the original value (or the capacitance curve rises to the maximum capacitance threshold from the original value, for example, C10 in FIG. 11B), it can be considered that electronic wetness-sensing absorbent article 10 has reached the maximum wetness degree, and a signal indicating that the absorbent article 10 needs to be replaced may be sent by the state displaying unit 38.

Further, the wireless receiver and state indicator 30 may further include a liquid excretion duration calculating unit 45 and a maximum liquid excretion time threshold storage unit 46. It is deemed that the liquid excretion time is unduly long (i.e., the urinating time is unduly long) if the curve still does not form an effective voltage valley value (or capacitance peak value) from the moment when one time of occurrence of wetting is determined to the time of the threshold (for example 10-300 s), which causes the electronic wetness-sensing absorbent article to enter a saturation state. In this case, a signal indicating that the absorbent article 10 needs to be replaced may be sent by the state displaying unit 38.

The wireless receiver and state indicator 30 may further include a processor 48, containing related functional modules controlling the wireless receiver and state indicator 30 and realizing related functions through combination of software and hardware. In an actual application, the wireless receiver and state indicator 30 may further be realized by adopting a smart phone in combination with an application program (App), i.e., the data information storage unit, the valid-wetting determining unit, the dry-state determining unit, the wet count calculating unit, the wet count threshold storage unit, the wet-state duration calculating unit, the maximum wait-time-to-dryness threshold storage unit, the wetness degree analyzing unit, the minimum voltage (or maximum capacitance) threshold storage unit, the liquid excretion duration calculating unit and the maximum liquid excretion time threshold storage unit are all disposed in the phone 30. In this case, the wetness state output unit 29 contains a device such as a Bluetooth transceiver or a Wi-Fi transceiver for communicating with the phone.

Figure 14:
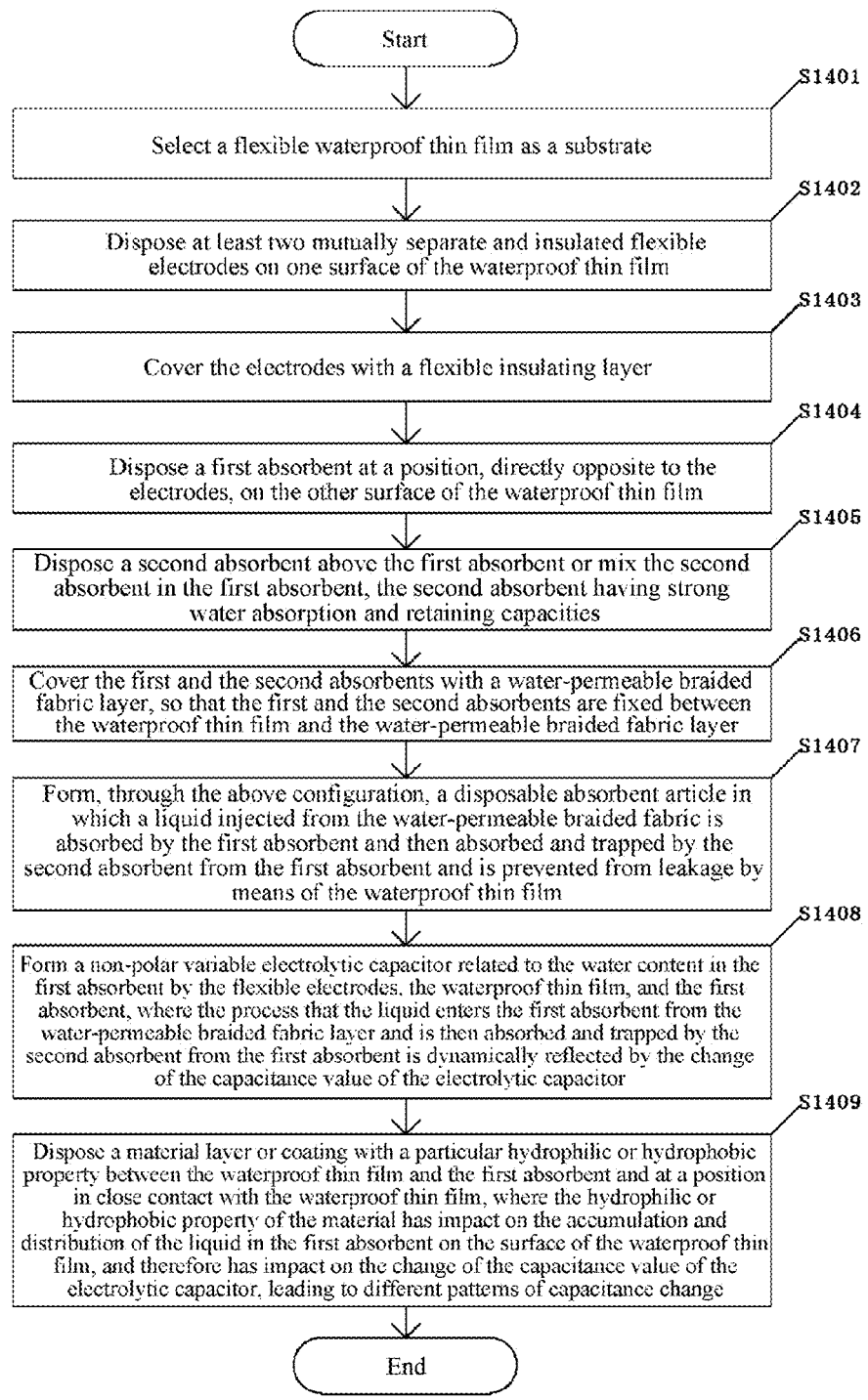
FIG. 14 is a flow chart of a method of manufacturing a disposable absorbent article capable of providing dynamic liquid absorption process information and absorption capacity information according to an embodiment of the present application.

Further, referring to FIG. 14, FIG. 14 is a flow chart of a method of manufacturing a disposable absorbent article capable of providing dynamic liquid absorption process information and absorption capacity information according to an embodiment of the present application, and is a summary of the method and device according to FIGS. 1-13 from a perspective of a manufacturing method. The method includes the following steps:

Step S1401: Select a flexible waterproof thin film as a substrate.

Step S1402: Dispose at least two mutually separated and insulated flexible electrodes on one surface of the waterproof thin film.

Step S1403: Cover the electrodes with a flexible insulating layer.

Step S1404: Dispose a first absorbent at a position, directly opposite to the electrodes, on the other surface of the waterproof thin film.

Step S1405: Dispose a second absorbent above the first absorbent or mix the second absorbent in the first absorbent, the second absorbent having strong water absorption and retaining capacities;

Step S1406: Cover the first and the second absorbents with a water-permeable braided fabric layer, so that the first and the second absorbents are fixed between the waterproof thin film and the water-permeable braided fabric layer.

Step S1407: Form, through the above configuration, a disposable absorbent article in which a liquid injected from the water-permeable braided fabric is absorbed by the first absorbent and then absorbed and trapped by the second absorbent from the first absorbent and is prevented from leakage by means of the waterproof thin film.

Step S1408: Form a non-polar variable electrolytic capacitor related to the water content in the first absorbent by the flexible electrodes, the waterproof thin film, and the first absorbent, where the process that the liquid enters the first absorbent from the water-permeable braided fabric layer and is then absorbed and trapped by the second absorbent from the first absorbent is dynamically reflected by the change of the capacitance value of the electrolytic capacitor.

Step S1409: Dispose a material layer or coating with a particular hydrophilic or hydrophobic property between the waterproof thin film and the first absorbent and at a position in close contact with the waterproof thin film, wherein the hydrophilic or hydrophobic property of the material has impact on the accumulation and distribution of the liquid in the first absorbent on the surface of the waterproof thin film, and therefore has impact on the change of the capacitance value of the electrolytic capacitor, leading to different patterns of capacitance change.

Figure 15:
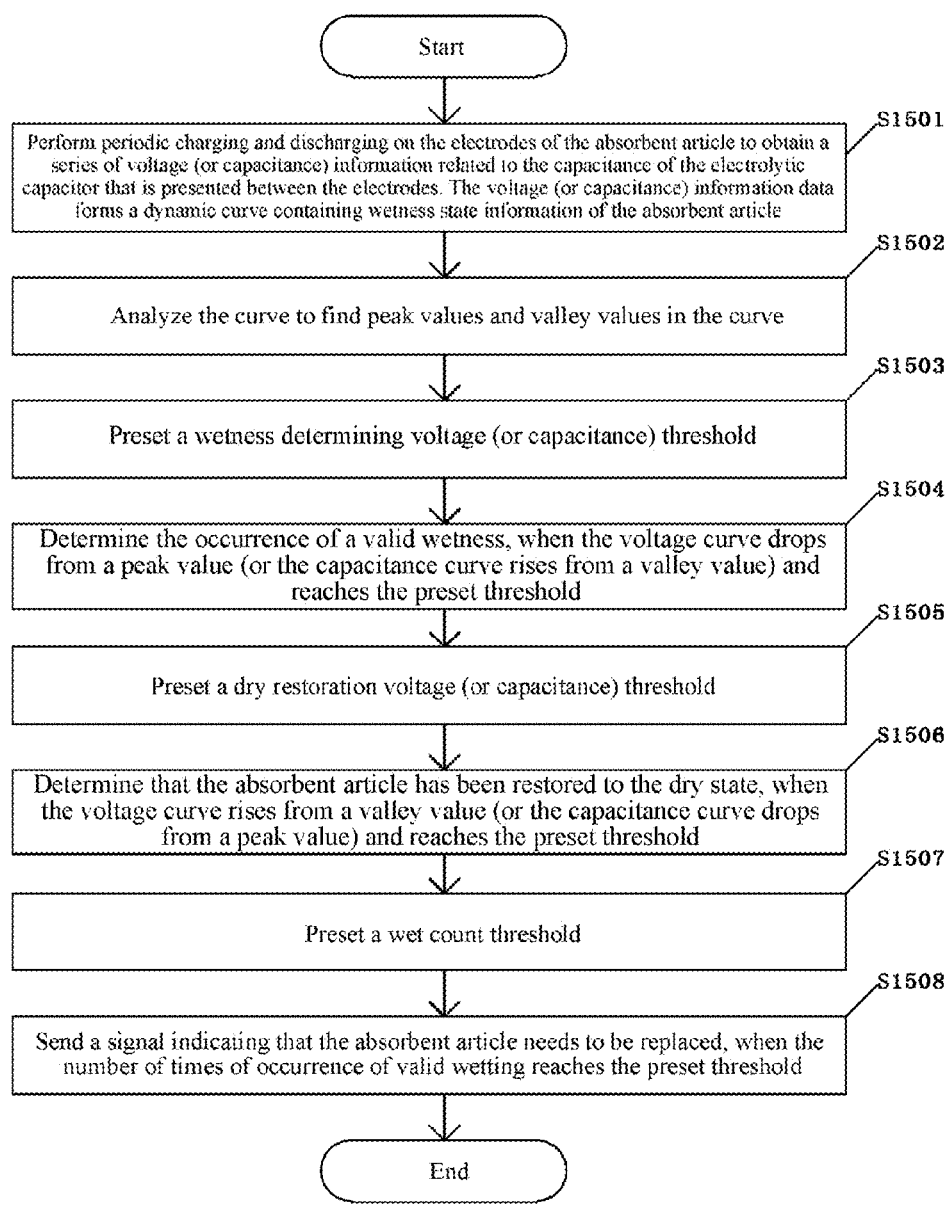
FIG. 15 is a flow chart of a method for realizing wetness analysis and state prompting on the basis of the electronic wetness-sensing absorbent article according to an embodiment of the present application.

Further, referring to FIG. 15, FIG. 15 is a flow chart of a method of realizing wetness analysis and state prompting on the basis of the electronic wetness-sensing absorbent article according to an embodiment of the present application, and the method flow includes the following steps:

Step S1501: Perform periodic charging and discharging on the electrodes of the electronic wetness-sensing absorbent article to obtain a series of voltage (or capacitance) information related to the capacitance value that is presented between the electrodes. The voltage (or capacitance) information data forms a dynamic information (voltage or capacitance) curve containing wetness state information of the electronic wetness-sensing absorbent article.

Step S1502: Analyze the curve to find information about peak values and valley values in the curve.

Step S1503: Preset a wetness determining voltage (or capacitance) threshold;

Step S1504: Determine the occurrence of a valid wetness when the voltage curve drops from a peak value (or the capacitance curve rises from a valley value) and reaches the preset threshold;

Step S1505: Preset a dry restoration voltage (or capacitance) threshold;

Step S1506: Determine that the electronic wetness-sensing absorbent article has been restored to the dry state, when the voltage curve rises from a valley value (or the capacitance curve drops from a peak value) and reaches the preset threshold.

Step S1507: Preset a wet count threshold; and

Step S1508: Send a signal indicating that the electronic wetness-sensing absorbent article needs to be replaced, when the number of times of occurrence of valid wetting reaches the preset threshold.

Figure 16:
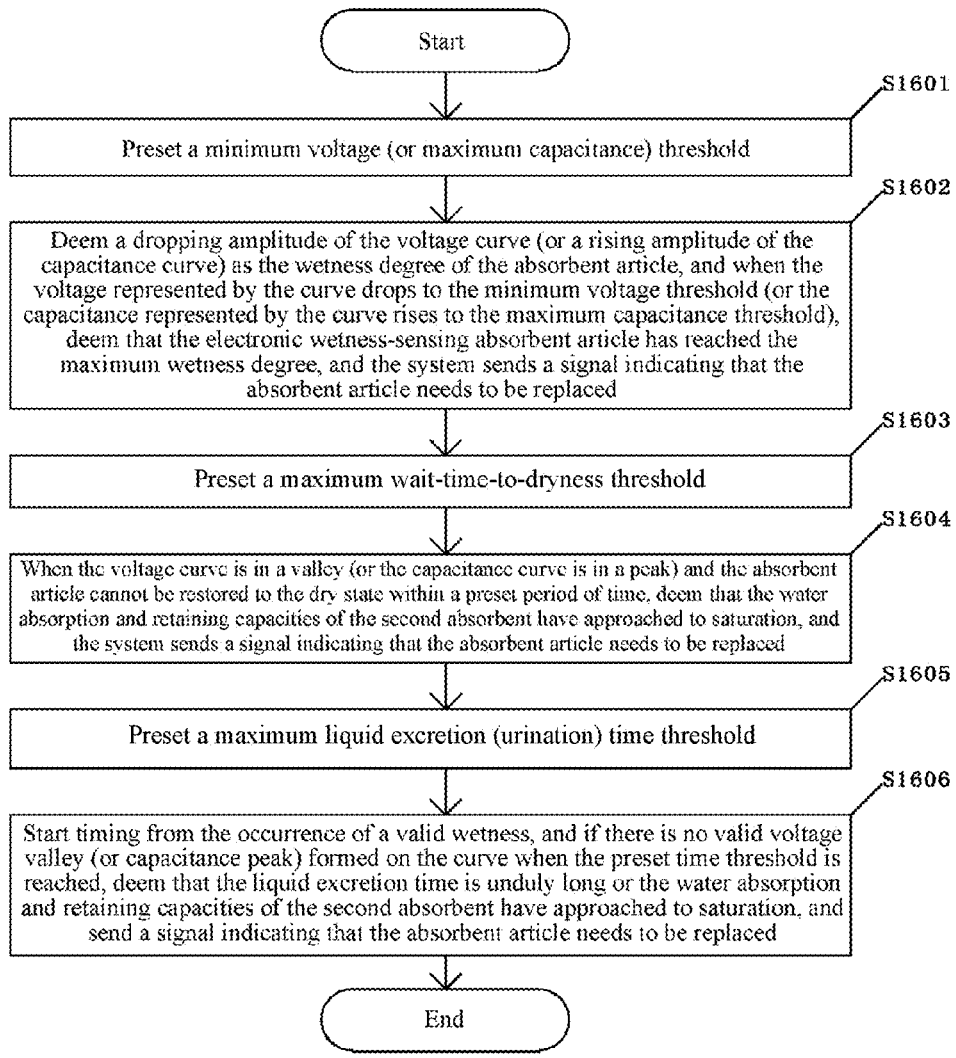
FIG. 16 is a flow chart showing another method for realizing wetness analysis and state prompting on the basis of the electronic wetness-sensing absorbent article according to an embodiment of the present application.

Further, referring to FIG. 16, FIG. 16 is another flow chart of a method of realizing wetness analysis and state prompting on the basis of the electronic wetness-sensing absorbent article according to an embodiment of the present application, and the method includes the following steps:

Step S1601: Preset a minimum voltage (or maximum capacitance) threshold.

Step S1602: Deem a dropping amplitude of the voltage curve (or a rising amplitude of the capacitance curve) as the wetness degree of the electronic wetness-sensing absorbent article, and deem that the electronic wetness-sensing absorbent article has reached the maximum wetness degree and send a signal indicating that the electronic wetness-sensing absorbent article needs to be replaced, when the voltage curve drops to the minimum voltage threshold (or the capacitance curve rises to the maximum capacitance threshold).

Step S1603: Preset a maximum wait-time-to-dryness threshold.

Step S1604: Deem that the water absorption and retaining capacities of the second absorbent have approached to saturation and send a signal indicating that the electronic wetness-sensing absorbent article needs to be replaced, when the voltage curve is in a valley (or the capacitance curve is in a peak) and the electronic wetness-sensing absorbent article cannot be restored to the dry state within a preset period of time.

Step S1605: Preset a maximum liquid excretion (urination) time threshold.

Step S1606: Start timing from the occurrence of a valid wetness, and if there is no valid voltage valley (or capacitance peak) formed on the curve when the preset time threshold is reached, deem that the excretion time is unduly long or the water absorption and retaining capacities of the second absorbent have approached to saturation, and send a signal indicating that the electronic wetness-sensing absorbent article needs to be replaced.

Figure 17:
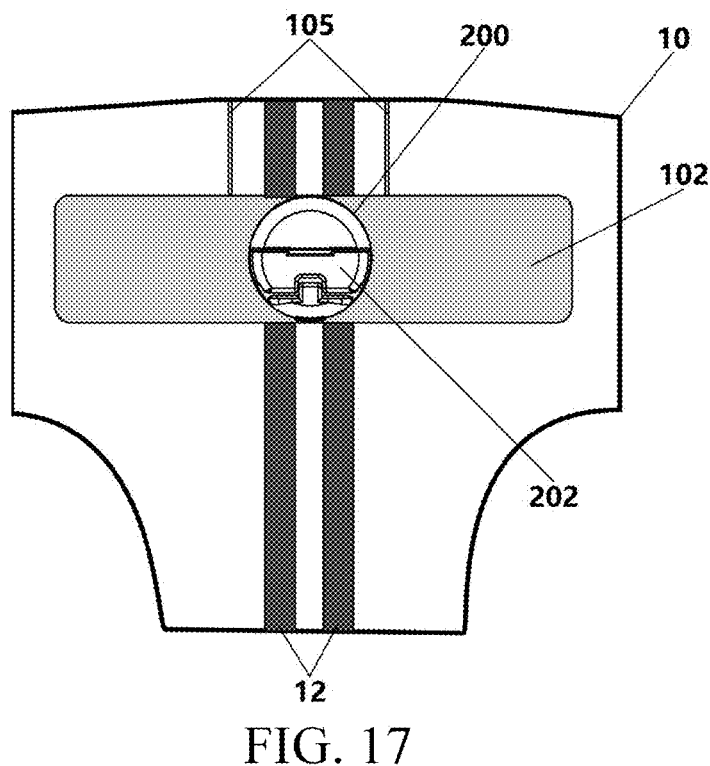
FIG. 17 is a schematic diagram of an appearance structure and an application of an electronic wetness sensing paper diaper according to an embodiment of the present application.

Further, referring to FIG. 17, FIG. 17 is a schematic diagram of an appearance structure and an application of an electronic wetness sensing paper diaper according to one embodiment of the present application. The paper diaper 10 is a specific application of foregoing electronic wetness-sensing absorbent article. The paper diaper 10 is provided with two flexible electrodes 12 formed by printing conductive ink. The flexible electrodes are also referred to as wetness sensing lines or sensing line electrodes here, the wetness sensing lines 12 are from the abdomen-side portion of the paper diaper 10 to the back waist part of the paper diaper 10 and extend across the whole paper diaper 10, such that urination occurring at different positions at the front and the rear of the paper diaper 10 can be sensed. The abdomen-side position of the paper diaper 10 includes an abdomen-side adhesive 102, which is generally made of a Velcro material, so as to conveniently adhere and tighten the waistline of the paper diaper 10.

In the embodiment of the present application, the abdomen-side adhesive 102 is further adapted to adhere the wetness detection device 200 that implements capacitance detection, and the urination state of the paper diaper 10 can be monitored in real time. The wetness detection device 200 includes a movable latch 202, capable of fixing a part of each of the wetness sensing lines 12 and being electrically connected to the wetness sensing lines 12, so as to detect the capacitance value of the generalized electrolytic capacitor formed by the paper diaper electrodes 12, the waterproof thin film 11 and the urine (electrolyte) and to learn the dynamic urination state change from the change of the capacitance value, thereby realizing the quantified wetness detection function. To conveniently fix the urination sensor 200 on the wetness sensing lines 12 of the paper diaper, two cuts 105 are formed at two sides of the wetness sensing lines 12 of the abdomen-side portion of the paper diaper 10 respectively, due to the presence of the cuts 105, the wetness sensing lines 12 between the cuts are overturned, and are electrically connected to the wetness detection device 120, thereby realizing the electronic wetness sensing function.

Figure 18:
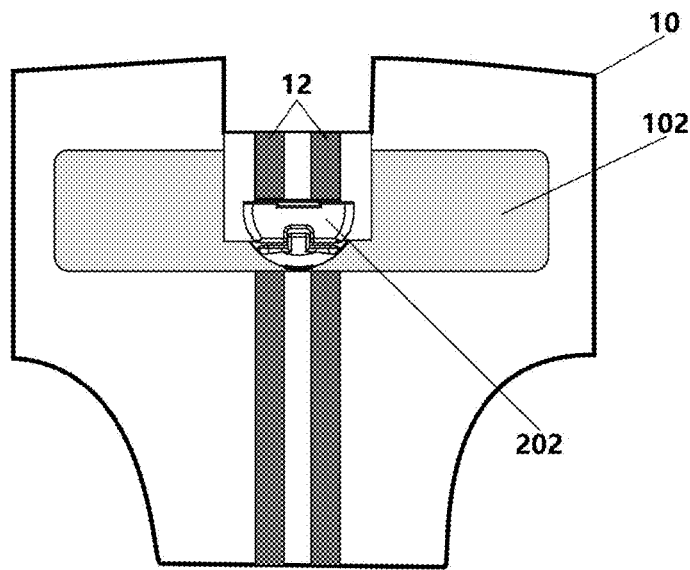
FIG. 18 is another schematic diagram of an appearance structure and an application of an electronic wetness sensing paper diaper according to an embodiment of the present application.

Further, referring to FIG. 18 below, FIG. 18 is another schematic diagram of an appearance structure and an application of an electronic wetness sensing paper diaper in one embodiment of the present application, and is further description on the foregoing FIG. 17. In FIG. 18, it can be seen that the wetness sensing lines 12 at the abdomen-side position of the paper diaper 10 can be overturned due to the presence of the cuts 105, can be fixed by the movable latch 202 of the wetness detection device, and then can be electrically connected to the wetness detection device 200, thereby realizing the electronic wetness sensing function.

Figure 19:
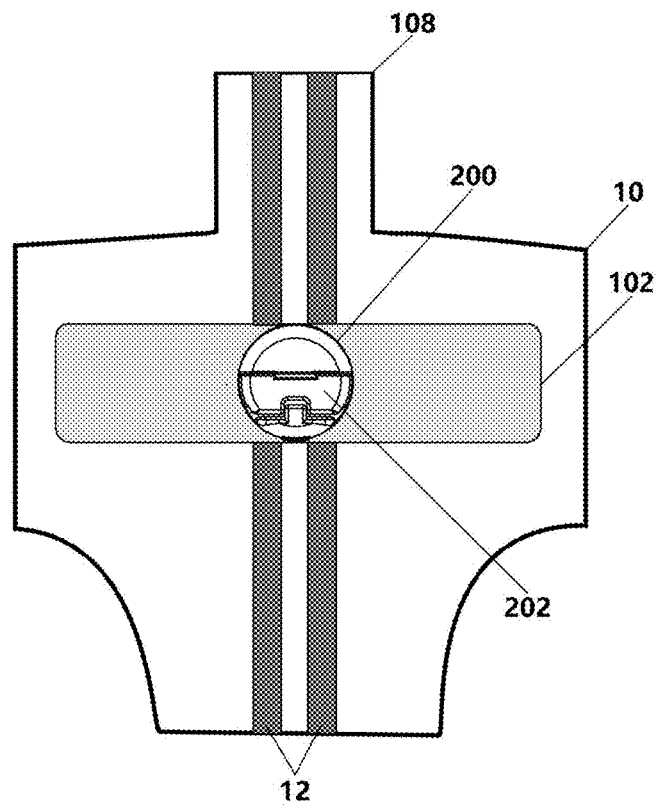
FIG. 19 is still another schematic diagram of an appearance structure and an application of an electronic wetness sensing paper diaper according to an embodiment of the present application.

Further, referring to FIG. 19, FIG. 19 is still another schematic diagram of an appearance structure and an application of an electronic wetness sensing paper diaper according to one embodiment of the present application, and is a change and innovation of the electronic wetness sensing paper diaper 10 according to the foregoing FIG. 17. Different from the structure that the paper diaper has two cuts 105 for conveniently overturning the wetness sensing lines 12 in FIG. 17, the position of the sensing lines at the abdomen-side portion of the paper diaper in FIG. 19 is provided with a projecting portion 108, which can be conveniently overturned to be electrically connected to the wetness detection device 200, thereby realizing the electronic wetness sensing function.

Figure 20:
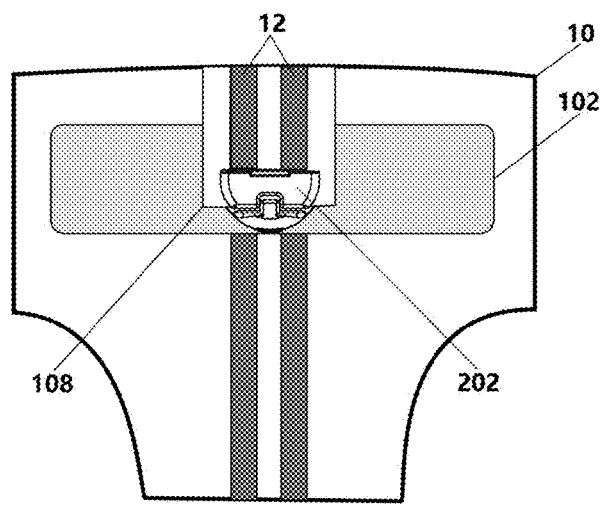
FIG. 20 is yet another schematic diagram of an appearance structure and an application of an electronic wetness sensing paper diaper according to an embodiment of the present application.

Further, referring to FIG. 20 below, FIG. 20 is yet another schematic diagram of an appearance structure and an application of an electronic wetness sensing paper diaper according to one embodiment of the present application, and is further description on the foregoing FIG. 19. In FIG. 17, it can be seen that the wetness sensing lines 12 at the abdomen-side position of the paper diaper 10 can be overturned due to the presence of the projecting portion 108, can be fixed by the movable latch 202 of the wetness detection device, and then can be electrically connected to the wetness detection device, thereby realizing the electronic wetness sensing function.

Figure 21:
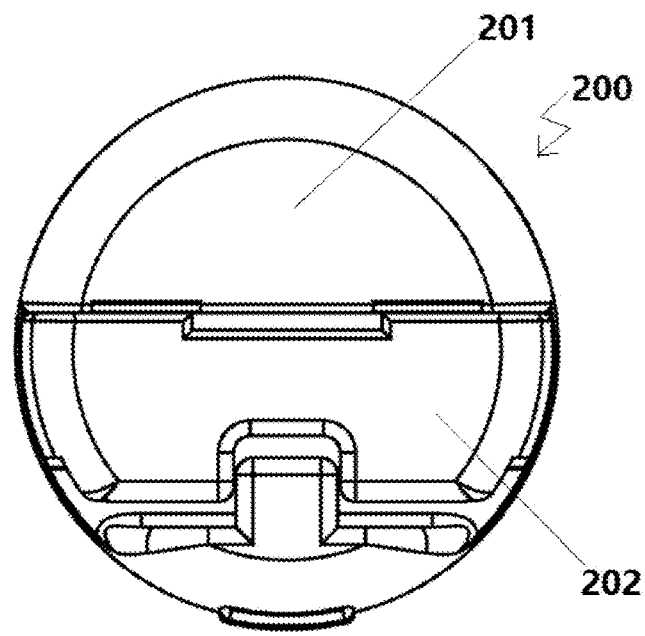
FIG. 21 is a front view of an appearance of a wetness sensing device according to an embodiment of the present application.

Further, referring to FIG. 21 below, FIG. 21 is a front view of an appearance of a wetness detection device according to an embodiment of the present application. In FIG. 21, 200 is the wetness detection device, including: a front housing 201 and a movable latch 202, where the movable latch can be opened and can fix the wetness sensing lines of the paper diaper. These functions are correspondingly described in foregoing FIGS. 17-20.

Figure 22:
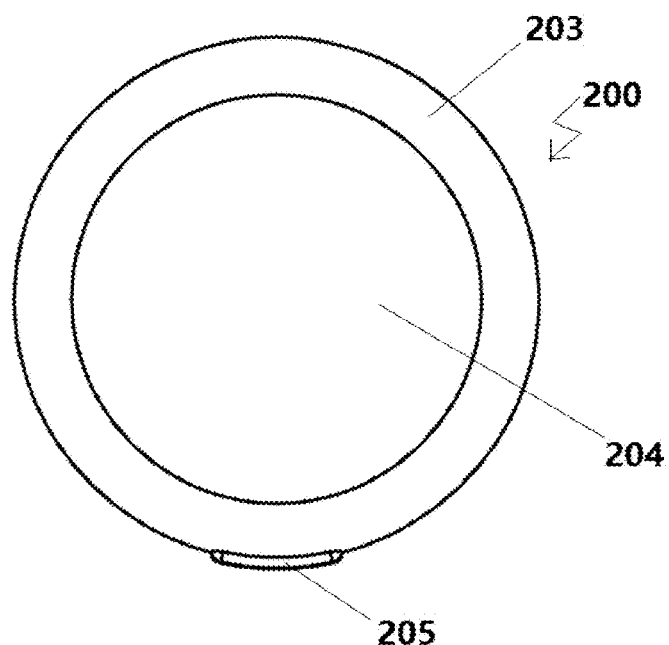
FIG. 22 is a rear view of an appearance of a wetness sensing device according to an embodiment of the present application.

Further, referring to FIG. 22, FIG. 22 is a rear view of an appearance of a wetness detection device according to an embodiment of the present application. In FIG. 22, 200 is the wetness detection device. A rear housing 203 can be seen from the rear view, the Velcro-tape 204 included on the rear housing 203 can adhesively fasten the wetness detection device 200 to the abdomen-side adhesive/Velcro-tape 102 of the paper diaper 10, so as to conveniently perform wetness detection on the paper diaper 10. In FIG. 22, it can be seen that a housing opening structure 205 is further included, which can separate/open the front housing 201 from/and the rear housing 203, so as to conveniently replace a button battery placed below the rear housing.

Figure 23:
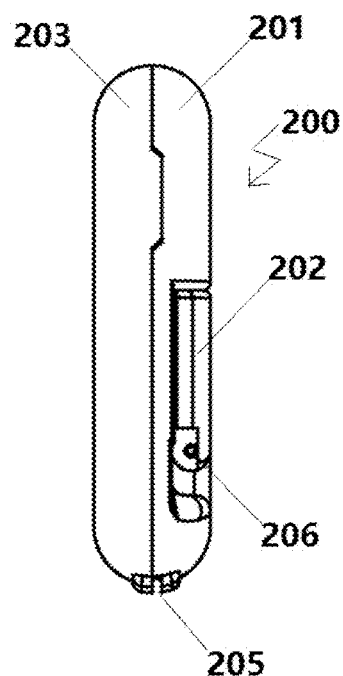
FIG. 23 is a left view of an appearance of a wetness sensing device according to an embodiment of the present application.

Further, referring to FIG. 23, FIG. 23 is a left view of an appearance of a wetness detection device according to an embodiment of the present application. In FIG. 23, 200 is the wetness detection device, the front housing 201 and rear housing 203 can be seen from the left view, the rear housing and front housing are combined together to form a sealed body. A sealed space of the sealed body includes an electronic circuit board, so as to conduct related functions including capacitance detection and wetness detection. The charging unit 23 (power source I), the discharging unit 24 (electronic switch K) and the voltage detection unit 25 included in the capacitance detection device 20 involved in the foregoing FIG. 10 and the charging and discharging unit 26, the digital-to-analog conversion unit 27, the processor 28 and the wetness state output unit (including a wireless transmitter/unit, a Bluetooth transceiver and a Wi-Fi transceiver) included in the wetness detection device 20 in FIG. 13 may be disposed on the electronic circuit board, so as to realize related functions, such as capacitance/wetness detection, data processing, signal analyzing, and signal transmission and output.

In an actual application, the button battery is adopted to provide power to related electronic parts and components/units/devices on the circuit board. There is a need to open the front housing and the rear housing, such that the user can replace the battery therein. To open the front housing and the rear housing, in the figure, a housing opening structure 205 is further included. The key of the housing opening structure 205 is a housing opening groove, through which an action force can be applied to open/separate the front housing and/from the rear housing, such that the user can conveniently replace the battery.

FIG. 23 further includes a movable latch 202 attached to the front housing 201. One end of the movable latch 202 includes a rotary shaft 206. The rotary shaft connects the front housing 201 and the movable latch 202 together, and allows the other end of the latch be opened at least by 90 degrees, such that the wetness sensing lines of the paper diaper can be conveniently fixed between the front housing 201 and the movable latch 202 and be locked.

Figure 24:
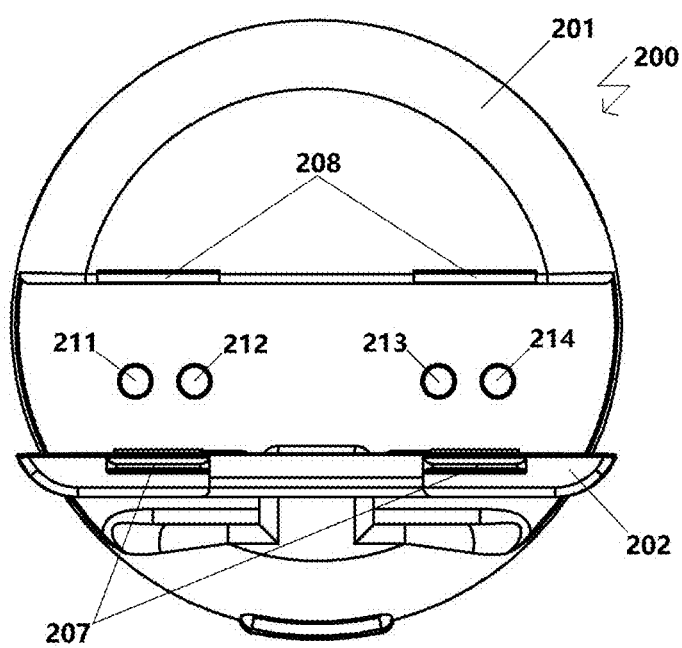
FIG. 24 is a schematic diagram of an application of a wetness sensing device according to an embodiment of the present application.

Further, referring to FIG. 24, FIG. 24 is a schematic diagram of an application of a wetness detection device 200 according to an embodiment of the present application. In FIG. 24, 201 is the front housing, and 202 is a movable latch after being opened by 90 degrees by taking the rotary shaft 206 as a center. The movable latch 202 includes a raised position 207. The front housing includes a groove 208 corresponding to the raised position 207. When the latch 202 is closed, the raised position 207 and the groove 208 are matched to lock the movable latch.

After the movable latch 202 is opened, four probes 211, 212, 213 and 214 disposed on the front housing can be seen, the probes are mainly adapted to be electrically connected to the wetness sensing lines 12 (including 121 and 122). In this embodiment, the reason of adopting 4 instead of 2 probes to connect the wetness sensing lines is mainly to realize a diaper-fastening detection function, i.e., detect and determine whether the paper diaper/nappy is tightly fastened by the movable latch, and whether the probes are in effect contact with the wetness sensing lines. In the probes, at least two probes function to detect the diaper-fastening, and when two probes are in contact with the same wetness sensing line at the same time (for example, 211 and 212 are in contact with 121, or 213 and 214 are in contact with 122 at the same time), the diaper-fastening detection unit connected to the other ends of the probes on the electronic circuit board will detect a related state, send a diaper-fastened signal, and turn on a related a light emitting diode (LED) indicator, so as to provide an indication of a diaper-fastening state.

In an actual application, the wetness detection device 200 adopts a waterproof design of a seal ring. The seal ring includes a housing seal ring, which is located between the front housing and the rear housing, and realizes a sealing function between the front housing and rear housing; and a probe seal ring, which is located between the probes and front housing, and realizes a sealing function between the probes and front housing. Due to the waterproof design, the sensor device can be conveniently cleaned and sterilized.

Since the wetness detection device 200 is applied by attaching to the abdomen-side position of the paper diaper, in an actual application, one sleep posture detection unit may be added in the electronic circuit board of the wetness detection device 200 to realize sleep posture detection of a user (for example, an infant) of the paper diaper. The infant sleep posture detection is very valuable in an actual application because research indicates that SIDS (Sudden Infant Death Syndrome) is related to a prone position condition of an infant, European and American countries began to propose to avoid the prone position of an infant from the end of the $20^{th}$ century (in particular, infants of 0-6 months old), so as to reduce the occurrence of SIDS.

In an actual application, a G-Sensor (gravity sensor) can be used to form the sleep posture detection unit. When an infant sleeps on his back, the front housing of the wetness detection device 200 faces upwards, the axis of a Z surface of the G-Sensor faces upwards accordingly and an axis upward signal is output; when the infant sleeps face down, the front housing of the wetness detection device faces downwards, the axis of the Z surface of the gravity sensor faces downwards accordingly, an axis downward signal is output, thereby identifying the sleep posture of the infant, and sending a related prompt/alarm signal.

Figure 25:
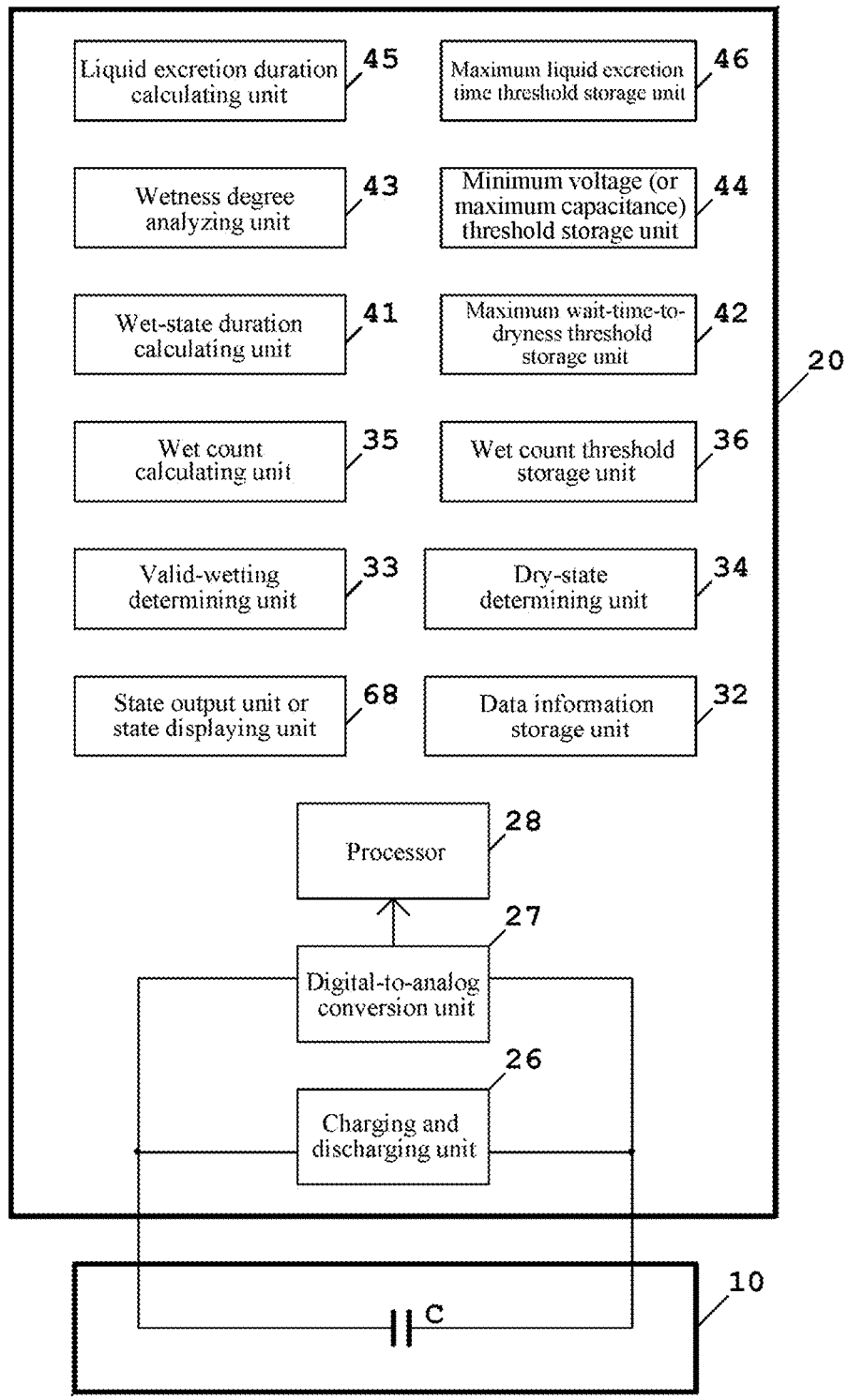
FIG. 25 is another schematic structural diagram of a wetness sensing device according to an embodiment of the present application.

In addition, according to the embodiment of the present application, more functions related to the wetness detection of the paper diaper 10 can be placed in the wetness detection device 20, or are integrated with the wireless receiver and state indicator 30 to form a device with more complete functions, so as to enable the wetness detection device 20 to include the data information storage unit, the valid-wetting determining unit, the dry-state determining unit, the wet count calculating unit, the wet count threshold storage unit, the wet-state duration calculating unit, the maximum wait-time-to-dryness threshold storage unit, the wetness degree analyzing unit, the minimum voltage (or maximum capacitance) threshold storage unit, the liquid excretion duration calculating unit and the maximum liquid excretion time threshold storage unit in the foregoing FIG. 13, and also include a state output unit or a state displaying unit 68 (which may include functions such as a urination data display function and a urination sound-light alarm function), thereby realizing the whole process from signal collecting to signal processing and then to state output or display, which is specifically shown in FIG. 25.

The present application shows the beneficial effects: by disposing the flexible electrodes and the absorbent layer for liquid absorption on the two sides of the flexible waterproof thin film of the electronic wetness-sensing absorbent article respectively, the flexible waterproof thin film, the flexible electrodes, and the liquid contained in the absorbent layer can form a variable electrolytic capacitor. The wetness state of the electronic wetness-sensing absorbent article can be obtained by only detecting the capacitance value of the capacitor and change thereof. In addition, by disposing the wetness detection device in the electronic wetness-sensing absorbent article, for example, in a paper diaper, the wetness sensing device performs periodic charging and discharging operations on the wetness sensing lines in the paper diaper by using the charging and discharging unit, obtains voltage peak value data (or capacitance value data) related to the variable capacitance value of the paper diaper, and forms a curve reflecting the wetness state of the paper diaper. The curve contains various information such as that for determining whether urination has occurred, how long the wet state lasts, how long the urination lasts, how many times the urination occurs, the maximum degree of wetness and whether the paper diaper has changed back to the dry state, making the wetness detection more diversified, such that the detection result contains more information.

The foregoing descriptions are merely exemplary embodiments of the present application, and certainly are not intended to limit the scope of claims of the present application. Therefore, equivalent variations made in accordance with the claims of the present application shall fall within the scope of the present application.

What is claimed is:

1. An electronic wetness-sensing absorbent article, comprising:
    a flexible waterproof thin film;
    at least two mutually separated and insulated flexible electrodes disposed on one surface of the flexible waterproof thin film;
    a water-permeable braided fabric layer; and
    an absorbent layer disposed on the other surface of the flexible waterproof thin film, located between the flexible waterproof thin film and the water-permeable braided fabric layer, and adapted to absorb a liquid entering from the water-permeable braided fabric layer, wherein:
    the flexible electrodes and the absorbent layer are located on the two surfaces of the flexible waterproof thin film respectively and are mutually separated and insulated from each other; and
    the flexible waterproof thin film, the flexible electrodes, and the liquid contained in the absorbent layer form a non-polar variable electrolytic capacitor, in which the flexible electrodes serve as electrodes of the electrolytic capacitor, the flexible waterproof thin film serves as a dielectric of the electrolytic capacitor, the liquid serves as an electrolyte of the electrolytic capacitor, and the wetness state of the electronic wetness-sensing absorbent article is obtained by detecting the capacitance value of the variable electrolytic capacitor and change thereof.

2. The electronic wetness-sensing absorbent article according to claim 1, wherein the absorbent layer comprises a first absorbent and a second absorbent mixed in the first absorbent, the first absorbent is adapted to absorb the liquid entering from the water-permeable braided fabric layer and thus increase the capacitance value of the variable electrolytic capacitor, and the second absorbent is adapted to absorb the liquid from the first absorbent and thus reduce the liquid content in the first absorbent and the wet area of the first absorbent, so as to reduce the capacitance value of the variable electrolytic capacitor.

3. The electronic wetness-sensing absorbent article according to claim 2, wherein the absorption rate of the first absorbent is faster than that of the second absorbent, the liquid absorption capacity of the second absorbent is higher than that of the first absorbent, and the second absorbent has water absorption and retaining capacities, such that a process that the liquid migrates from the first absorbent to the second absorbent is realized; the process is dynamically reflected by the change of the capacitance value; and the first absorbent comprises tiny water storage spaces formed by wood pulp or cotton pulp or a fluffy fabric or a flexible loose material, and the second absorbent comprises a tiny granular macromolecular water-absorbing resin.

4. The electronic wetness-sensing absorbent article according to claim 1, wherein:
    a hydrophilic layer is disposed between the flexible waterproof thin film and the absorbent layer and at a position in close contact with the flexible waterproof thin film, the hydrophilic layer is adapted to absorb the liquid from the absorbent layer and maintains the surface area of the liquid covering the flexible electrodes unchanged, such that the change of the capacitance value of the variable electrolytic capacitor is reduced, and the hydrophilic layer comprises any one or any combination of a hydrophilic material layer, a hydrophilic thin film, hydrophilic fibers, or a hydrophilic coating; and
    a surfactant is disposed between the hydrophilic layer and the flexible waterproof thin film.

5. The electronic wetness-sensing absorbent article according to claim 4, wherein the flexible waterproof thin film is a flexible waterproof gas-permeable thin film, an anti-permeation coating is disposed between the flexible waterproof gas-permeable thin film and the hydrophilic layer and at a position in close contact with the surface of the water-permeable film, and the anti-permeation coating is adapted to prevent the liquid contained in the hydrophilic layer from leaking through the waterproof gas-permeable thin film, so as to avoid short-circuiting between the mutually separated and insulated flexible electrodes.

6. The electronic wetness-sensing absorbent article according to claim 1, wherein the flexible waterproof thin film comprises a flexible insulating protective layer, covering the flexible electrodes and adapted to prevent the capacitance value of the electrolytic capacitor from being influenced when a human body touches the electrodes.

7. The electronic wetness-sensing absorbent article according to claim 1, wherein the flexible waterproof thin film comprises a polyethylene thin film.

8. The electronic wetness-sensing absorbent article according to claim 1 wherein the electronic wetness-sensing absorbent article is any one of a paper diaper, a nappy, a paper urine pad, or a sanitary napkin.

9. The electronic wetness-sensing absorbent article according to claim 1, wherein the flexible electrodes comprise wetness sensing lines, and the wetness sensing lines comprise those printed on the flexible waterproof thin film using a carbon-based conductive ink.

10. The electronic wetness-sensing absorbent article according to claim 9, further comprising a wetness detection device, electrically connected to the wetness sensing lines and adapted to detect the wetness state of the electronic wetness-sensing absorbent article, the wetness detection device comprising:
- a charging and discharging unit, adapted to perform periodic charging and discharging operations on the wetness sensing lines disposed on the paper diaper;
- a digital-to-analog conversion unit, adapted to obtain capacitance value data generated between the wetness sensing lines due to the periodic charging and discharging operations or voltage peak value data related to the capacitance value; and
- a processor, adapted to control the charging and discharging unit and the digital-to-analog conversion unit and process a series of voltage peak value data or capacitance value data to obtain quantified wetness state information.

11. The electronic wetness-sensing absorbent article according to claim 10, wherein the wetness detection device further comprises:
- a data information storage unit, adapted to store the series of voltage peak value data or capacitance value data and form a voltage curve or capacitance curve reflecting the wetness state of the electronic wetness-sensing absorbent article;
- a valid-wetting determining unit, adapted to determine whether wetting occurs once, according to a drop of the voltage curve from an original value or a peak value or a rise of the capacitance curve from an original value or a valley value; and
- a wetness state output unit, adapted to output wetness state information of the electronic wetness-sensing absorbent article.

12. The electronic wetness-sensing absorbent article according to claim 11, wherein the wetness detection device further comprises:
- a dry-state determining unit, adapted to determine whether the electronic wetness-sensing absorbent article has changed back to the dry state, according to a rise of the voltage curve from a valley value or a drop of the capacitance curve from a peak value;
- a wet count calculating unit, adapted to count the number of times of occurrence of wetting according to the output from the valid-wetting determining unit and output, when the number of times reaches a preset threshold, a signal indicating that the electronic wetness-sensing absorbent article needs to be replaced;
- a wet-state duration calculating unit, adapted to calculate a time from a valley of the voltage curve or from a peak of the capacitance curve, and output a signal indicating that the electronic wetness-sensing absorbent article needs to be replaced, if the electronic wetness-sensing absorbent article has not changed back to the dry state when the time exceeds a preset threshold;
- a wetness degree analyzing unit, adapted to determine a wetness degree of the electronic wetness-sensing absorbent article according to a dropping amplitude of the voltage curve or a rising amplitude of the capacitance curve, and output a signal indicating that the electronic wetness-sensing absorbent article needs to be replaced, when the change exceeds a preset threshold; and
- an excretion duration calculating unit, adapted to start timing from the occurrence of a valid wetness, and output a signal indicating that the electronic wetness-sensing absorbent article needs to be replaced, if there is no valid voltage valley or capacitance peak formed on the curve when a preset time threshold is reached.

13. The electronic wetness-sensing absorbent article according to claim 10, wherein the wetness detection device further comprises:
- a wireless transmission unit, adapted to send information related to the voltage peak value data in a wireless manner.

14. The electronic wetness-sensing absorbent article according to claim 10, wherein the electronic wetness-sensing absorbent article is a paper diaper, the paper diaper comprises an abdomen-side adhesive, the abdomen-side adhesive comprises a Velcro-tape adapted to adhere the wetness detection device, and cuts are formed on two sides of the wetness sensing lines at an abdomen-side portion of the paper diaper, such that the wetness sensing lines can be overturned by means of the cuts so as to electrically connect to the wetness detection device.

15. The electronic wetness-sensing absorbent article according to claim 10, wherein the electronic wetness-sensing absorbent article is a paper diaper, the paper diaper comprises an abdomen-side adhesive, the abdomen-side adhesive comprises a Velcro-tape adapted to adhere the wetness detection device, and the paper diaper comprises a projecting portion at the wetness sensing lines at the abdomen-side portion of the paper diaper, and the projecting portion is adapted to be overturned for electrically connecting the wetness sensing lines to the wetness detection device.

16. The electronic wetness-sensing absorbent article according to claim 10, wherein the wetness detection device further comprises:
- a rear housing, provided with a Velcro-tape adapted to adhesively fasten the wetness detection device to the electronic wetness-sensing absorbent article;
- a front housing, forming a sealed body together with the rear housing;
- an electronic circuit board, located inside the sealed body;
- a movable latch, adapted to tightly fasten the electronic wetness-sensing absorbent article in cooperation with the front housing; and
- probes, one end of each being located between the front housing and the movable latch, wherein when the electronic wetness-sensing absorbent article is tightly fastened, the probes are electrically connected to the wetness sensing lines on the electronic wetness-sensing absorbent article, so as to obtain a variable capacitance value signal provided by the electronic wetness-sensing absorbent article and send the variable capacitance value signal to the electronic circuit board.

17. The electronic wetness-sensing absorbent article according to claim 16, wherein the wetness detection device further comprises:
- a housing opening groove, through which the front housing can be separated from the rear housing for a battery replacement.

18. The electronic wetness-sensing absorbent article according to claim 16, wherein the wetness detection device further comprises:
- a housing seal ring, located between the front housing and the rear housing, and adapted to form a seal between the front housing and the rear housing; and
- a probe seal ring, located between the probes and the front housing, and adapted to form a seal between the probes and the front housing.

19. The electronic wetness-sensing absorbent article according to claim 16, wherein the wetness detection device further comprises:

a diaper-fastening detection unit, adapted to determine whether the electronic wetness-sensing absorbent article is tightly fastened by the movable latch, wherein when at least two of the probes are in contact with a same wetness sensing line at the same time, the diaper-fastening detection unit sends a diaper-fastened signal and turns on a light emitting diode (LED) indicator thereon.

20. The electronic wetness-sensing absorbent article according to claim 16, wherein the wetness detection device further comprises: a sleep posture detection unit, adapted to send a prone position signal when the wetness detection device is overturned.

21. A method of manufacturing a disposable absorbent article capable of providing dynamic liquid absorption process information and absorption capacity information, comprising the following steps:
selecting a flexible waterproof thin film as a substrate;
disposing at least two mutually separated and insulated flexible electrodes on one surface of the waterproof thin film;
covering the electrodes with a flexible insulating layer;
disposing a first absorbent at a position, directly opposite to the electrodes, on the other surface of the waterproof thin film;
disposing a second absorbent above the first absorbent or mixing the second absorbent in the first absorbent, the second absorbent having strong water absorption and retaining capacities, the first absorbent and the second absorbent forming an absorbent layer of the electronic wetness-sensing absorbent article;
covering the absorbent layer with a water-permeable braided fabric layer, so that the absorbent layer is fixed between the waterproof thin film and the water-permeable braided fabric layer;
forming, through the above configuration, a disposable absorbent article in which a liquid injected from the water-permeable braided fabric is absorbed by the first absorbent and then absorbed and locked by the second absorbent from the first absorbent and is prevented from leakage by means of the waterproof thin film; and
forming a special non-polar variable electrolytic capacitor by the electrodes, the waterproof thin film, and the liquid contained in the first absorbent, wherein the flexible electrodes serve as electrodes of the electrolytic capacitor, the waterproof thin film serves as a dielectric of the electrolytic capacitor, the liquid contained in the first absorbent serves as an electrolyte of the electrolytic capacitor; the capacitance value of the electrolytic capacitor is related to the content and distribution of the electrolyte contained in the first absorbent, and the process that the liquid enters the first absorbent from the water-permeable braided fabric layer and is then absorbed and locked by the second absorbent from the first absorbent is dynamically reflected by the change of the capacitance value of the electrolytic capacitor.

22. The manufacturing method according to claim 21, further comprising the following step:
disposing a material layer or coating with a particular hydrophilic or hydrophobic property between the waterproof thin film and the first absorbent and at a position in close contact with the surface of the waterproof thin film, wherein the hydrophilic or hydrophobic property of the material has impact on the accumulation and distribution of the liquid in the first absorbent on the surface of the waterproof thin film, and therefore has impact on the change of the capacitance value of the electrolytic capacitor, leading to the formation of different patterns of capacitance change and the content or distribution state of the liquid of the first absorbent is obtained by detecting the capacitance value of the capacitor.

23. The manufacturing method according to claim 22, wherein:
the first absorbent has a faster but lower absorption capacity, the liquid entering from the water-permeable braided fabric layer is firstly reflected by an increase in the liquid content in the first absorbent, such that the capacitance value of the electrolytic capacitor is increased;
the second absorbent has a slower but higher liquid absorption capacity, and captures the liquid from the first absorbent and locks the liquid, such that the water content in the first absorbent is reduced, and the capacitance value of the electrolytic capacitor is reduced, thus forming a dynamic change process that the capacitance value first increases and then decreases; and
the water absorption and retaining capacities of the second absorbent are limited, and the water absorption and retaining capacities decease significantly when approaching to saturation, such that the ability of the second absorbent to capture the liquid from the first absorbent is lowered, and the decreasing speed of the capacitance value is reduced, thereby providing information about whether the liquid absorption and retaining capacities of the electronic wetness-sensing absorbent article approach to a limit.

24. The manufacturing method according to claim 23, wherein the electronic wetness-sensing absorbent article comprises a disposable paper diaper, a nappy, a paper urine pad, and a sanitary napkin; the waterproof thin film comprises a polyethylene thin film; the water-permeable braided fabric comprises a nonwoven fabric and a hot air nonwoven fabric; the flexible electrodes comprise conductive ink lines printed on the waterproof thin film and metal lines adhered to the waterproof thin film; the insulating layer covering the electrodes comprises a soft and loose nonwoven fabric and a spunbonded fabric; the first absorbent comprises tiny water storage spaces formed by wood pulp or cotton pulp or a fluffy fabric or a particular flexible material, and the second absorbent comprises a tiny granular macromolecular water-absorbing resin mixed in the first absorbent or embedded in the tiny water storage spaces; the hydrophilic material comprises paper, cotton, and hydrophilic fibers; the hydrophobic material comprises a nonwoven fabric, hydrophobic fibers and a surfactant; and the liquid comprises urine, sweat, menstruation, or other water-containing excrements from human bodies or animals.

* * * * *